United States Patent [19]

Nagao et al.

[11] Patent Number: 4,918,184
[45] Date of Patent: Apr. 17, 1990

[54] AZETIDIN-2-ONE DERIVATIVES, AND PROCESS FOR PRODUCTION THEREOF USING TIN ENOLATES

[75] Inventors: Yoshimitsu Nagao, Uji; Toshio Kumagai, Kawagoe; Satoshi Tamai, Komae; Yasuhiro Kuramoto; Hisashi Shimidzu, both of Shiki, all of Japan

[73] Assignee: Lederle (Japan), Ltd., Tokyo, Japan

[21] Appl. No.: 137,089

[22] Filed: Dec. 23, 1987

Related U.S. Application Data

[62] Division of Ser. No. 901,127, Aug. 28, 1986, abandoned.

[30] Foreign Application Priority Data

Aug. 31, 1985 [JP] Japan ................................. 60-192905
Oct. 1, 1985 [JP] Japan ................................. 60-216127
Dec. 2, 1985 [JP] Japan ................................. 60-269417

[51] Int. Cl.⁴ ................. C07D 417/06; C07D 277/12; C07D 417/14; C07B 37/04
[52] U.S. Cl. .................................... 540/200; 548/188
[58] Field of Search ......................................... 540/200

[56] References Cited

U.S. PATENT DOCUMENTS 4,841,043 6/1989 Deziel ................................ 540/200

FOREIGN PATENT DOCUMENTS 0081817 6/1983 European Pat. Off. .

OTHER PUBLICATIONS

Nagao et al. I, "Chem. Abst." 105, col. 24221(k) (1986).
Nagao et al. II, "J. Org. Chem." 51(12) 2391-3 (1986).
Mukaiyama et al. I, "Chem. Abst." 101, col. 191759(r) (1984).
Iwasawa et al. I, "Chem. Abst." 98, col. 142907(y) (1983).
Nagao III; J. Amer. Chem. Soc. 108, 4673 1986 (7-3-1-86).
Iwasawa II, Chemistry Letters 1983, pp. 297-298.
Mukaiyama II, Tetrahedron 40, 1381 (1984).
Nagao IV, J.C.S. Chem. Comm 1985, 1418.

*Primary Examiner*—Mark L. Berch
*Attorney, Agent, or Firm*—Wenderoth, Lind & Ponack

[57] ABSTRACT

An azetidin-2-one derivative represented by the following formula (I)

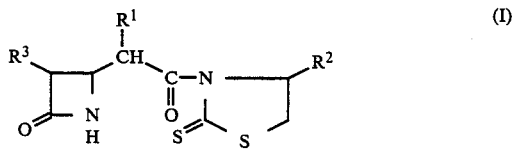

wherein $R^1$ represents a hydrogen atom, a lower alkyl group, an aryl group, an aralkyl group, a lower alkoxy group, aralkoxy group, a lower alkylthio group, an aralkylthio group, or a substituted amino group, $R^2$ represents a hydrogen atom, a lower alkyl group, an aryl group or an aralkyl group, and $R^3$ represents a hydrogen atom or a group of the formula

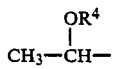

in which $R^4$ represents a hydrogen atom or a protective group for the hydroxyl group; and a process for production thereof.

10 Claims, No Drawings

AZETIDIN-2-ONE DERIVATIVES, AND PROCESS FOR PRODUCTION THEREOF USING TIN ENOLATES

This is a Rule 60 Divisional of Ser. No. 901,127, filed Aug. 28, 1986 now abandoned.

BACKGROUND OF THE INVENTION

1. Field of the Invention

This invention relates to azetidin-2-one derivatives, and a process for production thereof, and more specifically, to azetidin-2-one derivatives useful as intermediates for carbapenem-type antibiotics such as thienamycin or monocyclic beta-lactam antibiotics, and a process for production thereof.

2. Description of the Prior Art

It is well known that among beta-lactam anti-biotics, optically active compounds having a specific configuration have particularly good antimicrobial activity and beta-lactamase inhibiting activity. It has been strongly desired therefore to develop a process for producing such compounds.

Conventional methods for the production of optically active 4-substituted azetidin-2-one derivatives useful as synthesis intermediates for these beta-lactam antibiotics include, for example, (a) the utilization of natural amino acids such as L-aspartic acid [Hetero-cycles, 14, 1077 (1980)], and (b) the enzymatic hydrolysis of a prochiral beta-aminoglutaric acid diester to a half ester followed by cyclization [J. Am. Chem. Soc., 103, 2405 (1981)].

It may be feasible to use a different method which comprises using a 3-unsubstituted azetidin-2-one derivative having a leaving group at the 4-position as a starting material, and introducing a desired substituent stereoselectively into the 4-position of the starting material. For example, many prior attempts have been known in which these azetidin-2-one derivatives are reacted with various alkyl anions to alkylate the 4-position. All of them, however, are non-asymmetric methods, and none are directed to the production of optically active compounds [J. Chem. Soc., PT, 1981, 1884; Tetrahedron Letters, 22, 1161 (1981); Chem. Pharm. Bull., 28, 3494, 1980; J. Chem. Soc., Chem. Comm., 1981, 1076]. As a method of this type for stereoselectively introducing a 4-position substituent, Japanese Laid-Open Patent Publication No. 152866/1983 discloses a process for producing optically acive 4-phenyl-thioazetidin-2-one, which comprises reacting a 3-unsubstituted azetidin-2-one derivative with thiophenol in the presence of an optically active base (cinchonidine). According to this method, however, the substituent is not bonded to the 4-position directly through carbon.

On the other hand, many attempts have been made to alkylate the 4-position of a beta-lactam compound having a hydroxyethyl group at the 3-position of the beta-lactam ring and a leaving group at the 4-position thereof by reacting it with an alkylating agent, as schemcatically shown below.

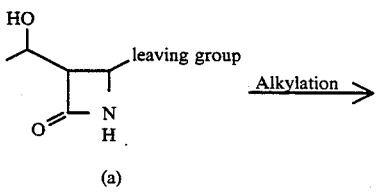

[A]

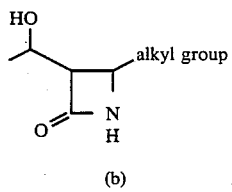

(b)

For the production of an optically active diastereomer of the compound (b) in this reaction scheme, a method is known which comprises preparing the optically active compound (a) from 6-aminopenicillic acid, L-aspartic acid or D-allothremin, and then stereoselectively introducing an alkyl group into the 4-position of the compound (a) [Chem. Pharm. Bull., 29, 2899, 1981; Tetrahedron Letters, 23, 2293, 1982; Tetrahedron Letters, 21, 4473, 1980; Tetrahedron Letters, 22, 5205, 1981].

Another method which may be feasible is to produce a racemate of the compound (b) in accordance with the reaction scheme (A) using a racemate of the compound (a) as a starting material and then converting its alkyl group to form carbapenem, etc., and to optically resolve the resulting compound in any of the steps.

In order to obtain carbapenem-series antibiotics having carba-2-penem-3-carboxylic acid of the following formula

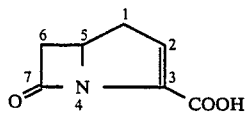

as a basic skeleton, it has previously been proposed to use the azetidin-2-one derivatives obtained by the aforesaid methods as starting materials. They include, for example, a compound having no substituent (the basic skeleton itself) [for example, J. Antibiotics, 35 (6), 653 (1982), JACS 100 (25), 8006 (1978)], compounds having substituents at the 2-position [for example, Tetrahedron Letters, 21, 2013 (1978)], compounds having substituents at the 6-position [for example, JACS 100 (25), 8004 (1978)], and thienamycin-series compounds having substituents at the 2- and 6-positions (for example, Japanese Laid-Open Patent Publications Nos. 87390/1978 and 32879/1983). These compounds basically have no substituent at the 1-position and show some degree of antimicrobial activity. Basically have no substituent at the 1-position.

On the other hand, as compounds having substituents at the 1-position, compounds having 1 or 2 substituents such as an alkyl, cycloalkyl, acyl, alkoxycarbonyl or cyano group at the 1-position have been reported (for example, Japanese Laid-Open Patent Publications Nos. 69586/1980, 130884/1984, 51286/1984, 93981/1982, and 84887/1984). Of these, (1R, 5S, 6S)-2-(2-N,N-dimethylamino-2-iminoethylthio)-6-[(1R)-1-hydroxyethyl]-1-methyl carba-2-penem-3-carboxylic acid having a beta-coordinated methyl group at the 1-position is known as an antibiotic having markedly improved resistance to decomposition and inactivation by kidney dehydropeptidase while carbapenem-series antibiotics are commonly susceptible to decomposition and inactivation by kidney dehydropeptidase [Heterocycles, 21(1), 29(1984)].

Although carbapenem-series antibiotics having various substituents at the 1-position either directly or through hetero atoms are expected to have excellent antimicrobial activity, they have not been investigated at all, and no method for production thereof has been developed.

SUMMARY OF THE INVENTION

Generally, the present invention provides important synthesis intermediates for the production of carbapenem-series antibiotics and monocyclic beta-lactam antibiotics which are expected to have strong antimicrobial activity and beta-lactamase inhibiting activity, and also a process for production thereof.

A first object of this invention is to provide azetidin-2-one derivatives represented by the following formula (I)

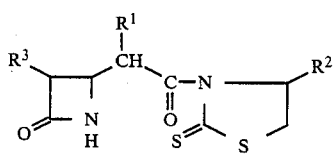

wherein $R^1$ represents a hydrogen atom, a lower alkyl group, an aryl group, an aralkyl group, a lower alkoxy group, aralkoxy group, a lower alkylthio group, an aralkylthio group, or a substituted amino group, $R^2$ represents a hydrogen atom, a lower alkyl group, an aryl group or an aralkyl group, and $R^3$ represents a hydrogen atom or a group of the formula

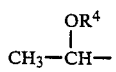

in which $R^4$ represents a hydrogen atom or a protective group for the hydroxyl group.

Accordingly, depending upon the presence of the substituent $R^3$ in formula (I), the present invention provides 3-unsubstituted azetidin-2-one derivatives represented by the following formula (Ia)

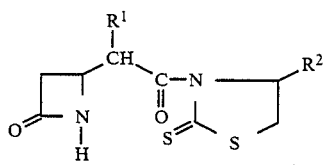

wherein $R^1$ and $R^2$ are as defined above, in one aspect, and 3-substituted azetidin-2-one derivatives represented by the following formula (Ib)

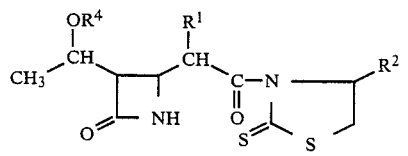

wherein $R^1$, $R^2$ and $R^3$ are as defined above, in another aspect.

One characteristic feature of this invention is to provide optically active azetidin-2-one derivatives of formula (I). Hence, the present invention provides compounds (I), (Ia) and (Ib) in which the substituents $R^1$, $R^2$, $R^3$ and $OR^4$ and the 4-position side chain have an R- or S-configuration.

Another object of this invention is to provide a process for producing the azetidin-2-one derivatives of formula (I).

Thus, according to this invention, there is provided a process for producing the azetidin-2-one derivatives of formula (I), which comprises reacting a compound represented by the following formula (II)

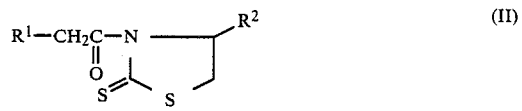

wherein $R^1$ and $R^2$ are as defined above, with tin (II) triflate in the presence of a base, and then reacting the resulting compound with a compound represented by the following formula (III)

wherein $R^3$ is as defined above, and L represents a lower alkanoyloxy group, a lower alkylsulfonyl group or an arylsulfonyl group.

More specifically, the process provided by this invention gives the azetidin-2-one derivatives represented by formula (Ia) or (Ib) by using a compound of the following formula (IIIa) or (IIIb)

depending upon the presence of the substituent $R^3$ in the compound of formula (III).

The present invention also provides a stereo-selective and stereospecific process for producing the azetidin-2-one derivatives of formula (I), and in formula (I), (Ia) or (Ib), the substituent $R^1$, $R^2$, $R^3$ and $OR^4$ and the 4-position side chain each have an R- or S-configuration.

In the process of this invention, a racemate of the compound of formula (IIIb) may also be used. Hence, the present invention also provides a process in which a threo-form racemate represented by the following formula (IIIc)

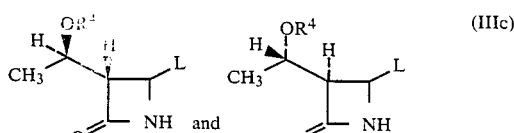

wherein L and R⁴ are as defined above, and an erythro-form racemate represented by the following formula (IIId)

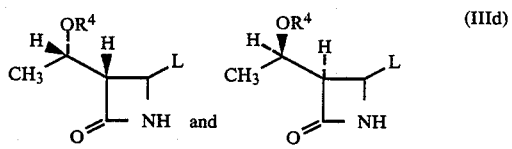

wherein L and R⁴ are as defined above, are used.

Still another object of this invention is to provide 1,3-thiazolidin-2-thione derivatives of formula (II)

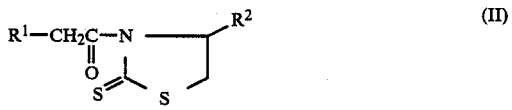

wherein R¹ and R² are as defined above, and particularly optically active 1,3-thiazolidin-2-thione derivatives in which R² has an R- or S-configuration.

DETAILED DESCRIPTION OF THE INVENTION

In the present specification and the appended claims, the "alkyl group" may be linear or branched, and may generally have 1 to 15 carbon atoms. Examples include methyl, ethyl, n-propyl, isopropyl, n-butyl, isobutyl, sec-butyl, tert-butyl, n-pentyl, isopentyl, n-hexyl, isohexyl, n-octyl, isooctyl, dodecyl and tetradecyl groups. Lower alkyl groups having up to 6 carbon atoms, preferably 1 to 4 carbon atoms, are suitable.

The "aryl group" is monocyclic or polycyclic and may have at least 1 alkyl group on the ring. Examples include phenyl, tolyl, xylyl, alpha-naphthyl, beta-naphthyl and biphenylyl groups.

The "aralkyl group" is an aryl-substituted alkyl group in which the alkyl and aryl groups have the above meanings. Specific examples include benzyl, phenethyl, α-methylbenzyl, phenylpropyl and naphthylmethyl groups.

The "aralkoxy group" and "aralkylthio group" are an aralkyl-O- group and an aralkyl-S- group in which the "aralkyl" moiety has the above meaning.

The "lower alkoxy group" and "lower alkylthio group" are an alkoxy group and an alkylthio group in which the alkyl moiety is the aforesaid lower alkyl group. Specific examples include methoxy, ethoxy, n-propoxy, isopropoxy, n-butoxy, isobtoxy, sec-butoxy and tert-butoxy groups; and methylthio, ethylthio, n-propylthio, isopropylthio and butylthio groups.

The "substituted amino group" means a mono- or di-substituted amino group. The substituent may, for example, be the alkyl group described above or an amino protective group. The "amino protective group" may include groups usually employed as protective groups for the amino group in peptide chemistry. Preferably, phthaloyl, benzyloxycarbonyl and t-butoxycarbonyl groups may be cited.

The "lower alkanoyloxy group" is a lower alkyl-CO-O-group in which the lower alkyl moiety has the above meaning. Examples include acetoxy, propionyloxy and butyryloxy groups.

The "arylsulfonyl group" is an aryl-SO₂- group in which the aryl moiety has the above meaning. Examples include benzenesulfonyl, tolylsulfonyl and naphthylsulfonyl groups.

The "lower alkylsulfonyl group" is a lower alkyl-SO₂- group in which the lower alkyl moiety has the above meaning. Specific examples include methanesulfonyl, ethanesulfonyl and propanesulfonyl groups.

The "protective groups for the hydroxyl group" represented by R⁴ may, for example, be a silyl group such as trimethylsilyl, triethylsilyl, tert-butyldimethylsilyl or diphenyl-tert-butylsilyl; a benzyloxycarbonyl group, a substituted benzyloxycarbonyl group such as p-nitrobenzyloxycarbonyl or o-nitrobenzyloxycarbonyl, and other protective groups for the hydroxyl group which are normally used.

The present invention provides the novel azetidin-2-one derivatives represented by formula (I). The present inventors noted that the compounds of formula (III) can be easily obtained, and have extensively worked in order to develop a process for producing 4-substituted azetidin-2-one derivatives having a substituent at the 4-position which are suitable for conversion to carbapenem-series antibiotics, etc. As a result, they have found that when the 1,3-thiazolidin-2-thione derivative of formula (II) is treated with tin (II) triflate in the presence of a base, and then reacted with the compound of formula (III), the substituent represented by L at the 4-position in the compound of formula (III) is stereoselectively replaced by a substituent of the following formula

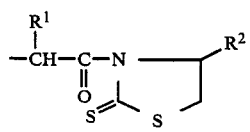

wherein R¹ and R² are as defined above, and the azetidin-2-one derivative of formula (I) can be obtained.

It has also been found that the side chain amide portion of the compound (I) obtained as above can be converted in good yields to various substituents suitable for conversion to carbapenem, etc., and also confirmed that the compound (I) provided by this invention is very useful as an intermediate for the production of carbapenem, etc.

It has further been found that when the compound of formula (II) used in the above reaction is a chiral 1,3-thiazolidin-2-thione derivative portion, the reaction proceeds stereoselectively to give an optically active azetidin-2-one derivative (I).

It has also been found that when a racemate of the compound of formula (III) is reacted with the chiral compound of formula (II), a diastereomeric mixture of the azetidin-2-one derivative represented by formula (I) is formed, and that this isomeric mixture can be easily separated by column chromatography and thin-layer chromatography and therefore the optically active azetidine-2-one derivative (I) can be produced.

When an optically active compound of formula (III) is used, an optically active azetidine-2-one derivative of formula (I) is obtained.

According to the present invention, optically active azetidine-2-one derivatives can be produced stereoselectively by using the chiral 1,3-thiazolidine-2-thione derivatives of formula (II). The characteristic feature of this invention is that the racemates of the optically active azetizine-2-one derivatives of formula (I) and if desired, their optically active forms can be stereoselectively produced.

The stereochemical characteristics of the invention will be described below with reference to, as an example, a process for producing an optically active compound of formula (I) which starts from (i) a 3-unsubstituted ($R^3$=H) compound of formula (III) and (ii) a 3-substituted

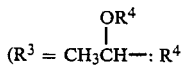
($R^3$ = $CH_3CH—$: $R^4$ (is as defined) compound of formula (III).

(i) When a compound of formula (III) in which $R^3$ is a hydrogen atom, i.e. a compound of the following formula (III-a), is used, the 4-position substituent is asymmetrically introduced by using an optically active compound of formula (II) as the other material. The configuration of the compound of formula (I) produced by the stereoselective process of this invention is shown by the following formula (I-a') or (I-a'') depending upon the configuration of the substituent $R^2$ in the optically active compound of formula (II) as an asymmetric source (see Reaction Scheme 1 below).

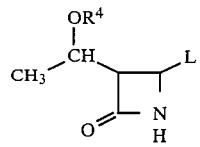
(III-b)

which correspond to the compound of formula (III) in which

$R^3$ is $CH_3CH—$ (wherein $R^4$ is as defined above), (ii-1) a racemate-thereof or (ii-2) an optically active form thereof may be used.

(ii-1) When the racemate of the compound of formula (III-b) is used, the use of the optically active compound of formula (II) leads to the production of an optically active 3,4-disubstituted azetidin-2-one derivative. Since in this reaction, a diastereomeric mixture is formed, it is necessary to separate the isomers by a suitable means. In order to make this separating operation easy and isolate

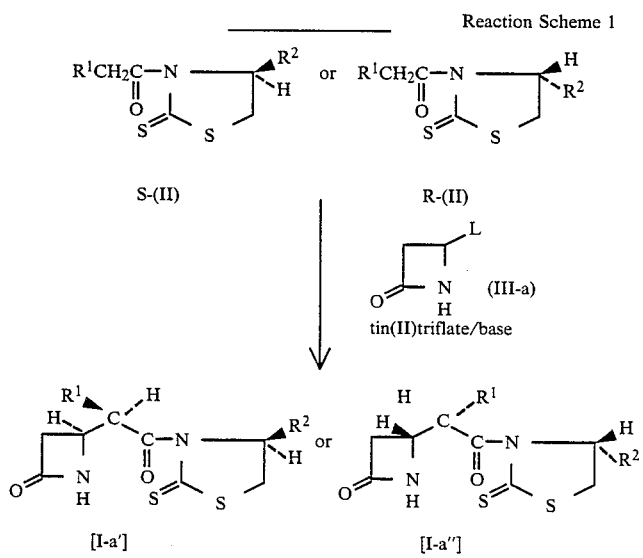

Reaction Scheme 1

In the formulae, $R^1$, $R^2$ and L are as defined hereinabove.

When the compound of formula (II) in which $R^2$ has an S-configuration is used in Reaction Scheme 1, the compound of formula (I) having the steric configuration shown in formula (1-a') forms as a main product. This reaction proceeds highly stereoselectively in high yields, and its marked characteristic feature is that not only the 4-position of the beta-lactam ring, but also the configuration of the $R^1$ substituent on the 4-position side chain are determined highly selectively, and the relative configuration is of erythro form.

(ii) As a compound represented by the following formula the desired isomers in high purity, the compound of formula (III-b) is preferably used in a (1',3)-threo form (III-c) and a (1',3)-erythro form (III-d)

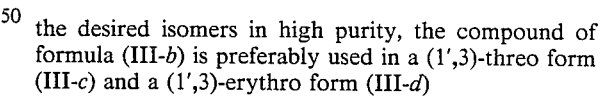

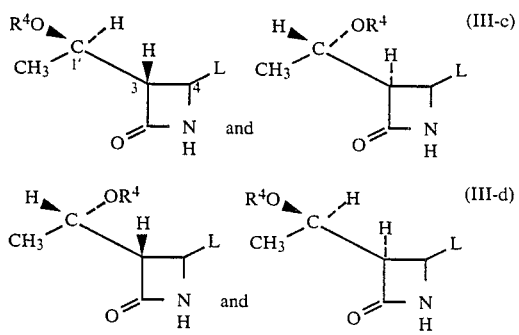

separated in advance. In the compounds of formulae (III-c) and (III-d), the 4-position substituent L may have any configuration. Specifically, it may be cis-or trans-to the 3-position. Usually, the trans-isomer is frequently used.

When the compound of formula (III-c) and the S-form of the compound of formula (II) are used, a mixture of three diastereomers of formulae (I-c), (I-d) and (I-e) is obtained mainly in accordance with Reaction Scheme 2 below.

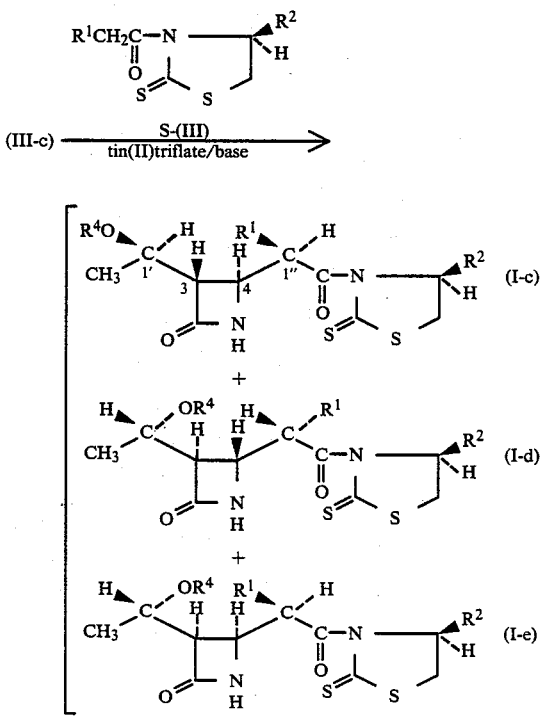

The amounts of the isomers in the mixture formed by the above reaction are generally (I-c)>(I-d)>(I-e) in decreasing order, and a compound having a specific configuration [the compound of formula (I-c) in this example] is formed especially advantageously. Furthermore, a compound of formula (I) in which the configuration of (4,1″) is of erythro form is formed specifically.

On the other hand, when the compound of formula (III-d) and the S-form of the compound of formula (II) are used, the amounts of isomers formed in accordance with Reaction Scheme 3 are (I-f)>(I-g>(I-h) in decreasing order, and the compound of formula (I-f) is formed advantageously.

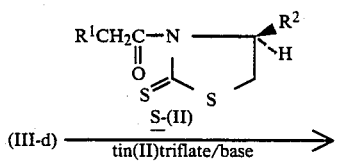

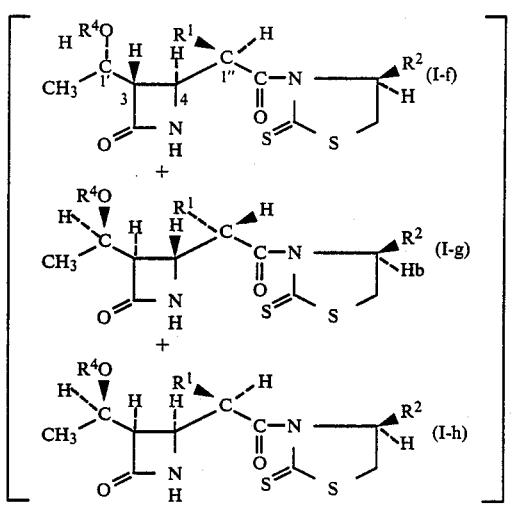

In the formulae, $R^1$, $R^2$ and $R^4$ are as defined above.

The resulting diastereomeric mixtures can be very easily separated into the individual isomers. This is another advantage of this invention. The compounds of formula (I) are yellow, and can be separated, for example, by column chromatography or thin-layer chromatography. The positions of the individual isomers can be easily determined visually on the chromatogram. This is very advantageous to the separating operation.

In the example of (ii-1), the optically active compound of formula (II) can be said to be a kind of optical resolving agent for the compound of formula (III). But unlike ordinary resolving agents, it performs alkylation and resolution simultaneously. In addition, since this alkylation is carried out asymmetrically, the use of the optically active compound (II) would be very unique in that an isomer having a specific configuration is formed especially advantageously.

(ii-2) When an optically active compound of formula (III-b) is used, a compound of formula (II) in which $R^2$ is a hydrogen atom may be used as a first means. In other words, even when the compound of formula (II) ($R^2=H$) is reacted with the optically active compound of formula (III-c), the compound of formula (I) can be produced stereoselectively in accordance with Reaction Scheme 4 below.

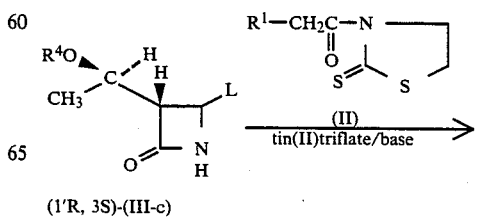

-continued
Reaction scheme 4

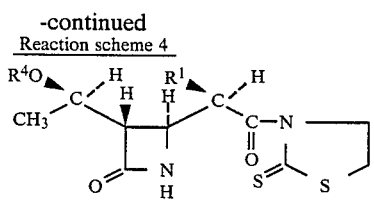

(I)

In the above formulae, $R^1$, $R^4$ and L are as defined above.

As a second means, however, the stereoselectivity can be further enhanced by using a compound of formula (II) in which $R^2$ is a substituent other than hydrogen.

For example, a compound of formula (I-c) can be produced highly stereoselectively in accordance with Reaction Scheme 5 below using an optically active compound of formula (III-c) (1'R, 3S-form) and an S-form of the compound of formula (II).

Reaction scheme 5

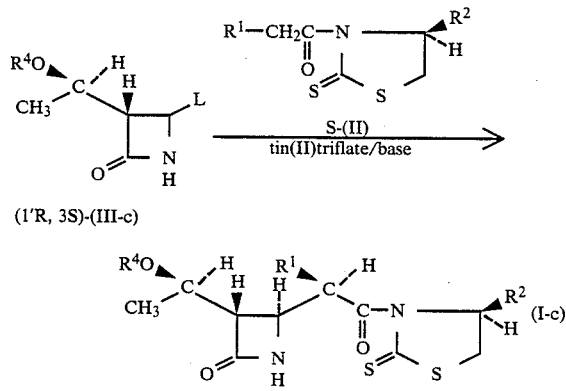

In the formulae, $R^1$, $R^2$, $R^4$ and L are as defined hereinabove.

As shown above, the present invention has been accomplished by using a tin (II) enolate of the compound of formula (II) as a reagent for the compound of formula (III). The thiazolidine-2-thionamide portion of the compound of formula (II) is not only essential to the reaction but also plays an important role in the final compound of formula (I). Firstly, since the compound having this structural portion is yellow, isolation and purification of the product can be carried out very easily. Secondly, since this structural portion is a so-called "active amide" structure, it serves to produce other derivatives, and because of this, the compounds of formula (I) provided by this invention are very useful as intermediates for the synthesis of carbapenem-series antibiotics or monocyclic beta-lactam antibiotics.

For example, the compound of formula (I-c) has a thienamycin-type configuration when $R^1$ is a hydrogen atom. When $R^1$ is a methyl group, the compound of formula (I-c) is useful as an intermediate for the synthesis of carbapenems such as MK-591 type carbapenem [Hetero-cycles, 21(1), 29 (1984)]. When such a carbapenem is to be synthesized from the compound of formula (I-f) above, the configuration of the hydroxyl group in the 3-position side chain can be reversed by a customary method such as the Mitsunobu's method.

A further advantage of the present invention is that the optically active compound of formula (I) has an active amide structure. For example, the 1,3-thiazolidine-2-thione derivative portion can be used immediately for derivation of thienamycin, etc. For example, by subjecting the compound of formula (I-c) to reaction either directly or through a carboxylic acid (IV), it can be converted to a useful synthesis intermediate (V) such as thienamycin, as shown by the following formula [B].

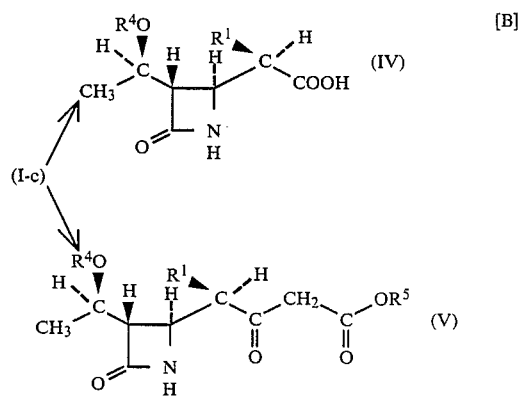

In the formulae, $R^1$ and $R^4$ are as defined hereinabove, and $R^5$ represents a lower alkyl group or an unsubstituted or substituted aralkyl group.

As shown above, in the process of this invention, the compound of formula (II) may be said to be a kind of optical resolving agent for the compound of formula (III), but unlike ordinary resolving agents, it has various characteristics as shown below, and is very unique.

(1) It induces alkylation and resolution simultaneously. Since alkylation is carried out asymmetrically, an optically active compound having a specific configuration is formed especially advantageously.

(2) The resulting diastereomeric mixture can be very easily resolved.

(3) The 1,3-thiazolidine-2-thione portion in the resolving agent (II) is useful for the production of other derivatives, and the optically active 1,3-thiazolidine-2-thione derivative which leaves can be recovered and reused. The acyl portion can be used as part of the structure of the final desired product such as thienamycin.

Accordingly, this invention also provides a 1,3-thiazolidine-2-thione derivative of formula (II) which is specific for the optical resolving agent.

The process of this invention will be described in more detail hereinafter.

As the starting compound of formula (III), the 3-unsubstituted compound (III-a) and the 3-substituted compound (III-b) are selected. They are subjected to the reaction after as required the hydroxyl group of the compound III-b is protected. A silyl group such as t-butyldimethylsilyl group is conveniently used as such a protective group. Silylation is carried out in a customary manner. Typically, the compound is treated with a silylating agent such as t-butyldimethylchlorosilane in a suitable inert solvent such as tetrahydrofuran, dichloromethane, chloroform, dichloroethane, acetonitrile, ethyl acetate or dimethylformamide, either alone or in combination, in the presence of a base such as triethylamine, diisopropylethylamine or imidazole, preferably triethylamine, usually at a temperature of −20 to 25° C.

for a period of 0.5 to 24 hours. As a result, a silyl-protected compound can be obtained.

According to the process of this invention, the compound of formula (II) is first reacted with tin (II) triflate in the presence of a base to form an enolate. The enolate is then reacted with the compound of formula (III) to form the desired azetidin-2-one derivative.

The enolation reaction of the N-acyl-1,3-thiazolidin-2-thione derivative of formula (II) with tin (II) triflate can be conveniently carried out usually in an inert solvent.

Examples of the solvent include ethers such as diethyl ether and tetrahydrofuran, hydrocarbons such as toluene, xylene and cyclohexane, and halogenated hydrocarbons such as dichloromethane and chloroform. Tetrahydrofuran is especially preferred.

The reaction temperature is not strictly limited, and may be varied widely according to the starting material used. Generally, it is about −100° C. to room temperature, preferably about −78° C. to about 0° C.

The amount of tin (II) triflate relative to the compound of formula (II) is not critical. Usually, tin (II) triflate is used in an amount of about 1 to about 2 moloes, preferably 1 to 1.5 moles, per mole of the compound of formula (II).

The enolation reaction is carried out in the presence of a base. It is, for example, a tertiary amine such as triethylamine, diisopropylethylamine, 1,4-diazabicyclo[2.2.2]octane, N-methylmorpholine, N-ethylpiperidine or pyridine. Of these, N-ethylpiperidine is used advantageously. The proportion of the base is about 1.0 to about 3 equivalents, preferably 1.0 to 2.0 equivalents, per mole of the compound of formula (II).

The enolation reaction can be terminated generally in about 5 minutes to about 4 hours to form an enolate.

Subsequently to the enolation reaction, the resulting enolate is directly reacted with the compound of formula (II).

The alkylation reaction between the enolate and the compound of formula (II) may be carried out at a temperature of from about −100° C. to room temperature, preferably about −78° C. to about 10° C. The amount of the compound of formula (II) is not critical, and may be varied. Usually, it is used in an amount of about 0.5 to about 5 moles, preferably 0.5 to 2 moles, per mole of the compound of formula (II), used in the enolation reaction.

Under these conditions, the reaction is generally terminated in about 5 minutes to about 5 hours, more generally about 5 minutes to about 2 hours.

Preferably, the enolation reaction and the alkylation reaction are carried out in an inert atmosphere, for example in an atmosphere of nitrogen gas or argon gas.

Finally, the reaction product is treated with water. For example, after the reaction, a phosphate buffer having a pH of about 7 is added to the reaction mixture, and the insoluble materials are separated by filtration. The compound of formula (I) may be isolated and purified in a customary manner, for example by extraction, recrystallization or chromatography.

Resolution of the resulting diastereomeric mixture into optically active isomers can be carried out efficiently by ordinary column chromatography using silica gel or the like, or thin-layer chromatography. The isomers obtained by the process of this invention are yellow substances and can be very easily distinguished on a chromatogram. The amount of the carrier (if it is silica gel) is usually about 20 to 100 g per gram of the diastereomeric mixture.

Typical examples of the compound of formula (I) so obtained are shown in the following table.

TABLE 1

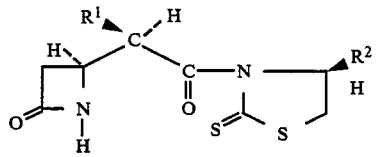
(I-a')

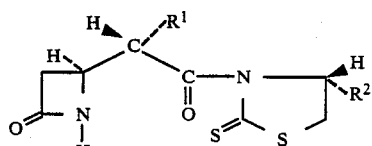
(I-a'')

| $R^1$ | $R^2$ |
|---|---|
| H | $CH_3$ |
| H | $CH_2CH_3$ |
| H | $CH(CH_3)_2$ |
| H | $CH_2CH(CH_3)_2$ |
| H | $C_6H_5$ |
| H | $CH_2C_6H_5$ |
| $CH_3$ | $CH_3$ |
| $CH_3$ | $CH_2CH_3$ |
| $CH_3$ | $CH(CH_3)_2$ |
| $CH_3$ | $CH(CH_3)CH_2CH_5$ |
| $CH_3$ | $C_6H_5$ |
| $CH_3$ | $CH_2C_6H_5$ |
| $CH_2CH_3$ | $CH_2CH_3$ |
| $CH_2CH_3$ | $CH_2CH(CH_3)_2$ |
| $CH_2CH_2CH_3$ | $CH(CH_3)_2$ |
| $C_6H_5$ | $CH_2CH_3$ |
| $CH_2C_6H_5$ | $CH_2CH_3$ |
| $CH_2C_6H_5$ | $CH_2CH(CH_3)_2$ |
| $CH_2CH_2C_6H_5$ | $CH_2CH_3$ |

TABLE 2

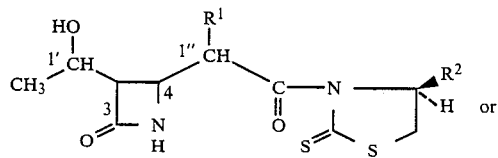

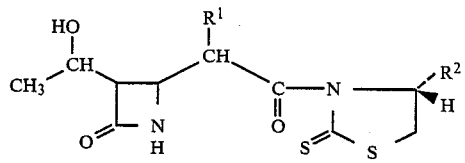

| R¹ | R² | 1' | 3 | 4 | 1'' |
|---|---|---|---|---|---|
| H | H | R | S | R | — |
| H | H | S | R | S | — |
| H | C₂H₅ | R | S | R | — |
| H | C₂H₅ | S | R | S | — |
| H | C₂H₅ | S | R | R | — |
| H | C₂H₅ | S | S | R | — |
| H | C₂H₅ | R | S | S | — |
| H | C₂H₅ | R | R | R | — |
| H | CH(CH₃)CH₃ | R | S | R | — |
| H | CH(CH₃)CH₃ | S | R | S | — |
| H | CH(CH₃)CH₃ | S | R | R | — |
| H | C₆H₅ | S | S | R | — |
| H | C₆H₅ | R | R | S | — |
| H | C₆H₅ | R | R | R | — |
| CH₃ | H | R | S | R | R |
| CH₃ | H | S | R | S | S |
| CH₃ | C₂H₅ | R | S | R | S |
| CH₃ | C₂H₅ | S | R | S | R |
| CH₃ | C₂H₅ | S | R | R | R |
| CH₃ | C₂H₅ | S | S | R | R |
| CH₃ | C₂H₅ | R | S | S | S |
| CH₃ | C₂H₅ | R | R | R | R |
| CH₃ | CH(CH₃)CH₃ | R | S | R | R |
| CH₃ | CH(CH₃)CH₃ | S | R | S | S |
| C₆H₅ | CH(CH₃)CH₃ | R | S | R | R |
| C₆H₅ | CH(CH₃)CH₃ | S | R | S | S |
| C₆H₅ | CH(CH₃)CH₃ | S | R | R | R |
| CH₂C₆H₅ | C₂H₅ | S | S | R | R |
| CH₂C₆H₅ | C₂H₅ | R | R | S | S |
| CH₂C₆H₅ | C₂H₅ | R | R | R | R |
| H | CH₂C₆H₅ | R | S | R | — |
| H | CH₂C₆H₅ | S | R | S | — |
| H | CH₂C₆H₅ | S | R | R | — |
| H | CH₃ | R | S | R | — |
| H | CH₃ | S | R | S | — |

TABLE 2-continued

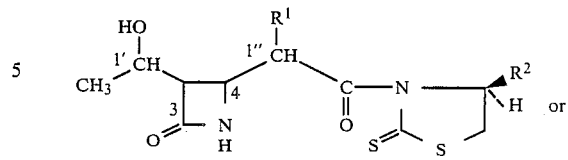

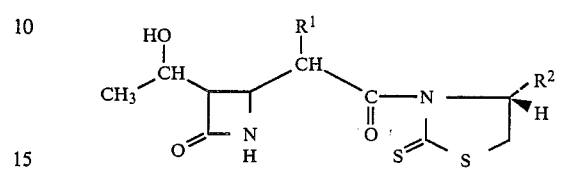

| R¹ | R² | 1' | 3 | 4 | 1'' |
|---|---|---|---|---|---|
| H | CH₃ | S | R | R | — |
| CH(CH₃)CH₃ | C₂H₅ | R | S | R | R |
| CH(CH₃)CH₃ | C₂H₅ | S | R | S | S |
| CH(CH₃)CH₃ | C₂H₅ | S | R | R | R |

TABLE 3

| R¹ | R² | R³ |
|---|---|---|
| CH₃O | H | H |
| CH₃S | H | H |
| C₆H₅CH₂S | H | H |
| C₆H₅CH₂O | H | H |
| Z-NH*¹ | H | H |
| Pht=N*² | H | H |
| CH₃O | C₂H₅ | H |
| CH₃O | CH(CH₃)CH₃ | H |
| CH₃S | CH(CH₃)CH₃ | H |
| C₂H₅S | C₂H₅ | H |
| C₂H₅O | C₂H₅ | H |
| C₂H₅O | CH₃ | H |
| CH₃O | C₆H₅CH₂ | H |
| C₆H₅CH₂O | CH(CH₃)CH₃ | H |
| C₆H₅CH₂S | CH(CH₃)CH₃ | H |
| C₆H₅CH₂O | C₂H₅ | H |
| C₆H₅CH₂O | C₆H₅ | H |

TABLE 3-continued

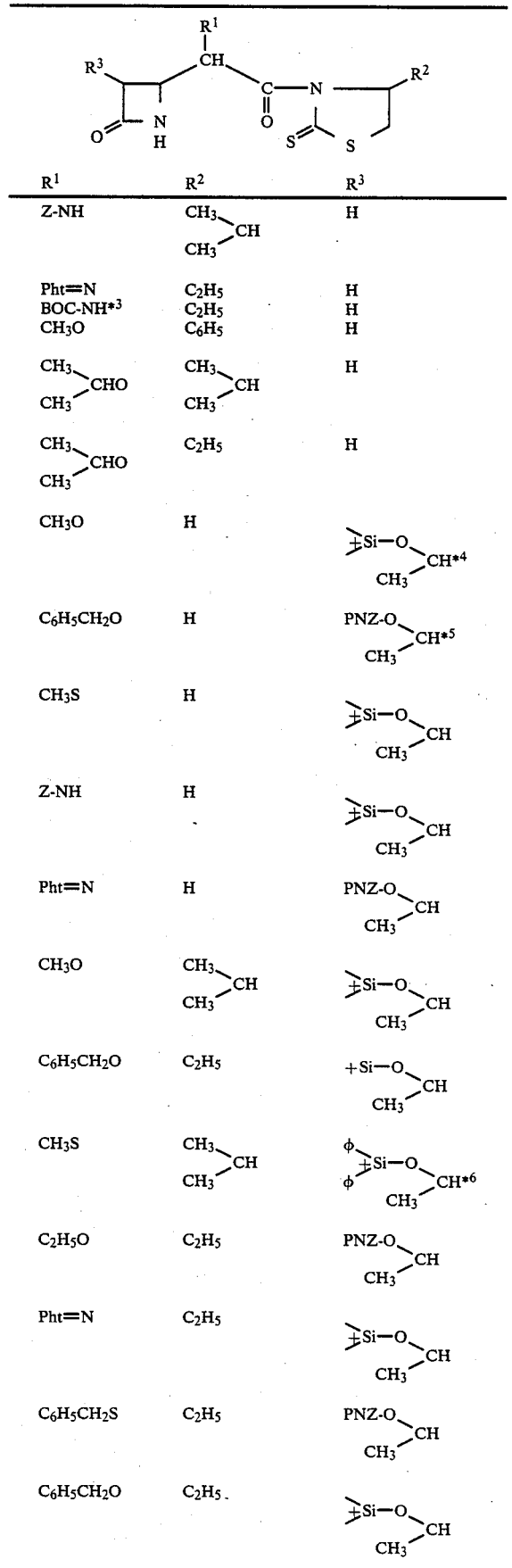

| R¹ | R² | R³ |
|---|---|---|
| Z-NH | $CH_3$-CH-$CH_3$ | H |
| Pht=N | $C_2H_5$ | H |
| BOC-NH*3 | $C_2H_5$ | H |
| $CH_3O$ | $C_6H_5$ | H |
| $CH_3$-CHO-$CH_3$ | $CH_3$-CH-$CH_3$ | H |
| $CH_3$-CHO-$CH_3$ | $C_2H_5$ | H |
| $CH_3O$ | H | ≢Si-O-CH-$CH_3$ *4 |
| $C_6H_5CH_2O$ | H | PNZ-O-CH-$CH_3$ *5 |
| $CH_3S$ | H | ≢Si-O-CH-$CH_3$ |
| Z-NH | H | ≢Si-O-CH-$CH_3$ |
| Pht=N | H | PNZ-O-CH-$CH_3$ |
| $CH_3O$ | $CH_3$-CH-$CH_3$ | ≢Si-O-CH-$CH_3$ |
| $C_6H_5CH_2O$ | $C_2H_5$ | +Si-O-CH-$CH_3$ |
| $CH_3S$ | $CH_3$-CH-$CH_3$ | φ-Si-O-CH-$CH_3$ *6 |
| $C_2H_5O$ | $C_2H_5$ | PNZ-O-CH-$CH_3$ |
| Pht=N | $C_2H_5$ | ≢Si-O-CH-$CH_3$ |
| $C_6H_5CH_2S$ | $C_2H_5$ | PNZ-O-CH-$CH_3$ |
| $C_6H_5CH_2O$ | $C_2H_5$ | ≢Si-O-CH-$CH_3$ |

TABLE 3-continued

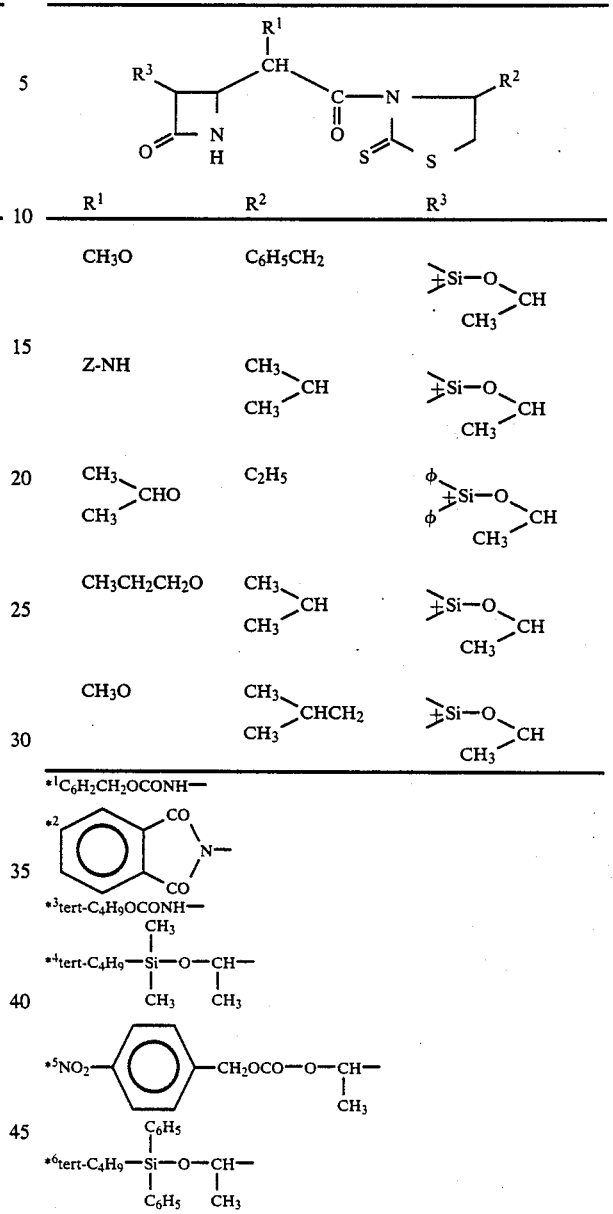

| R¹ | R² | R³ |
|---|---|---|
| $CH_3O$ | $C_6H_5CH_2$ | ≢Si-O-CH-$CH_3$ |
| Z-NH | $CH_3$-CH-$CH_3$ | ≢Si-O-CH-$CH_3$ |
| $CH_3$-CHO-$CH_3$ | $C_2H_5$ | φ-Si-O-CH-$CH_3$ |
| $CH_3CH_2CH_2O$ | $CH_3$-CH-$CH_3$ | ≢Si-O-CH-$CH_3$ |
| $CH_3O$ | $CH_3$-CHCH_2-$CH_3$ | ≢Si-O-CH-$CH_3$ |

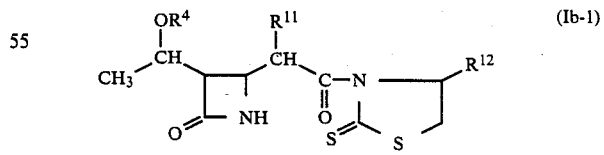

Of the compounds of formula (I) provided by this invention, an especially preferred group of compounds are azetidin-2-one derivatives of the following formula $$\text{(Ib-1)}$$

wherein $R^{11}$ represents an alkyl group having 1 to 4 carbon atoms, or an alkoxy group having 1 to 4 carbon atoms, $R^{21}$ represents a hydrogen atom or an alkyl group having 1 to 4 carbon atoms, and $R^4$ is as defined above.

The compounds of formula (I) provided by this invention are useful as intermediates for synthesis of carbapenem-series antibiotics and monocyclic beta-lactamseries antibiotics. For example, various derivatives useful as synthesis materials for carbapenems can be produced from the compounds of formula (I) by the following method.

For example, with regard to compounds of formula (I-a) corresponding to a compound of formula (I) in which $R^3$ is hydrogen, the production of various derivatives from the compound of formula (I-a) will be described. In this case, the compound of formula (I-a) is subjected to a reaction after, as required, its ring nitrogen is protected. As protective groups trimethylsilyl, triethylsilyl, t-butyldimethylsilyl, and diphenyl-t-butylsilyl groups are used. The t-butyldimethylsilyl group is especially preferably used. Silylation reaction is carried out in a customary manner. Typically, the compound of formula (I-a) is treated with a silylation agent such as t-butyldimethylchlorosilane in a suitable inert solvent such as tetrahydrofuran, dichloromethane, chloroform, dichloroethane, acetonitrile, ethyl acetate and dimethylformamide, either singly or in combination, in the presence of a base such as triethylamine, diisopropylethylamine or imidazole, preferably triethylamine, usually at a temperature of about $-20°$ to about $25°$ C. for about 0.5 to about 24 hours.

Reduction of an optically active compound (VI-a) [including the compound of formula (I-a) and its silyl derivatives] in accordance with the following reaction scheme C gives an optically active alcohol of formula (VII-a).

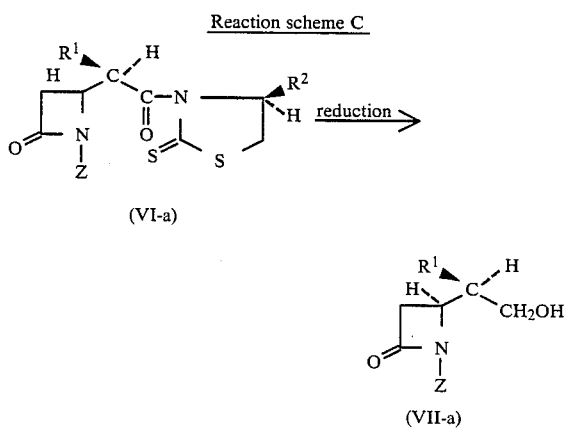

(In the formulae, $R^1$ and $R^2$, and Z represents a hydrogen atom or a silyl protective group.

Suitable reducing agents used in this reduction include, for example, boron hydride/metal complexes such as lithium borohydride, sodium borohydride, lithium triisobutylborohydride, potassium sec-butylborohydride and sodium tri-sec-butylborohydride; and substituted borohydrides such as trimethylaminoborane. Of these, sodium borohydride is preferred. Ususlly, this reduction is carried out in a solvent, for example an ether such as diethyl ether, diisopropyl ether, ethylene glycol dimethyl ether, tetrahydrofuran or dioxane, an alcohol such as methanol, ethanol or isopropanol; and water. The amount of the reducing agent used is not critical, but suitably it is usually 0.25 to 5 moles per mole of the compound of formula (VI-a). The reaction temperature is about $-50°$ about $100°$ C., preferably about $-30°$ to about $20°$ C. The reaction time differs depending upon the solvent, the reducing agent, the reaction temperature, etc., but usually a period of from 10 about minutes to about 2 hours is sufficient.

From the resulting optically active alcohol of formula (VII-a) (when Z is a silyl protective group, after it is split off in a customary manner), a compound of formula (VII-a) useful as an intermediate for the production of carbapenems such as thienamycin can be produced by the method described in the literature (Japanese Laid-Open Patent Publication No. 69586/1980) as shown by the following reaction scheme D.

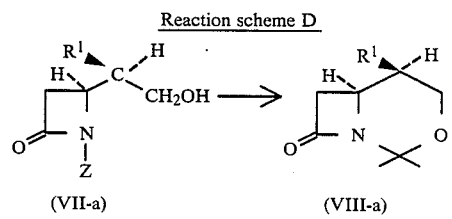

(In the formulae, $R_1$ and Z are as defined above.)

From the compound of formula (VI-a), a compound of formula (IX-a) may be produced by extending two carbon atoms in accordance with the following reaction scheme E.

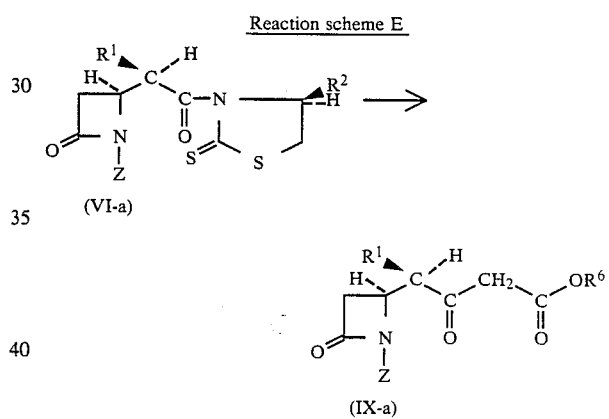

(In the formulae, $R^1$, $R^2$ and Z are as defined above, and $R^6$ represents an ester residue.)

This can be carried out by
(i) reacting the compound of formula (VI-a) with an acetic ester in the presence of a base,
(ii) reacting it with a magnesium salt of a half ester of malonic acid, or (iii) reacting it with Meldrum's acid. For example, the reaction (i) may be effected by reacting 1 mole of the acetic ester with 0.85 to 1.1 moles of the compound of formula (VI-a) in the presence of 1 to 2 moles, per mole of the acetic ester, of a base such as methyllithium, butyllithium, sec-butyllithium, phenyllithium, lithium diisopropylamide or lithium hexamethylenedisilazane, preferably lithium diisopropylamide. This reaction is carried out usually in a solvent such as diethyl ether, tetrahydrofuran, dimethoxyethane or dimethylformamide. The reaction temperature is usually in the range of about $-100°$ to about $0°$ C. The reaction time may be 1 to 30 minutes. The reaction (ii) is effected by reacting 1 to mole of the compound of formula (IV-a) with 1 to 3 moles of a magnesium salt of a half ester of malonic acid represented by the following formula

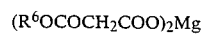 (X)

wherein $R^6$ represents an ester residue, in the same solvent as described with regard to (i) generally at a temperature of about 0° to about 50° C. for about 1 to 50 hours.

Examples of the ester residue represented by $R^6$ are ordinary carboxy protecting groups, for example lower alklyl groups such as methyl, ethyl, n-propyl, isopropyl, sec-butyl and t-butyl and substituted or unsubstituted aralkyl groups such as benzyl, p-nitrobenzyl and o-nitrobenzyl.

The compound of formula (VI-a) may be easily converted into the corresponding ester (XIa) by treating it with (i) a metal alcoholate, or with (ii) an alcohol in the presence of a base in accordance with the following reaction scheme E.

Reaction scheme F

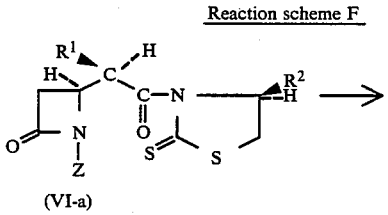

(VI-a)

(XI-a)

(In the formulae, $R^1$, $R^2$ and Z are as defined above, and $R^6$ represents an ester residue.)

The method in accordance with (i) is carried out by treating the compound of formula (VI-a) usually in a solvent such as tetrahydrofuran, dimethoxyethane or dimethylformamide with 1 to 2 moles, per mole of the compound (VI-a), of a sodium or potassium alkoxide of an alcohol corresponding to the desired ester, such as methanol, ethanol or benzyl alcohol. It is proper to carry out the reaction usually at a temperature of about 0° to about 25° C. for about 0.5 to 3 hours. On the other hand, the method in accordance with (ii) proceeds smoothly at a reaction temperature of about 0° to 25° C. by treating the compound of formula (VI-a) with a large amount of an alcohol in the presence of a base such as sodium hydroxide, potassium hydroxide or potassium carbonate.

A carboxylic acid of the following formula (XII) can be produced (a) by directly hydrolyzing the compound of formula (VI-a), or (b) by removing the ester residue from the compound of formula (XI) by a suitable technique, in accordance with the following reaction scheme G.

Reaction Scheme G

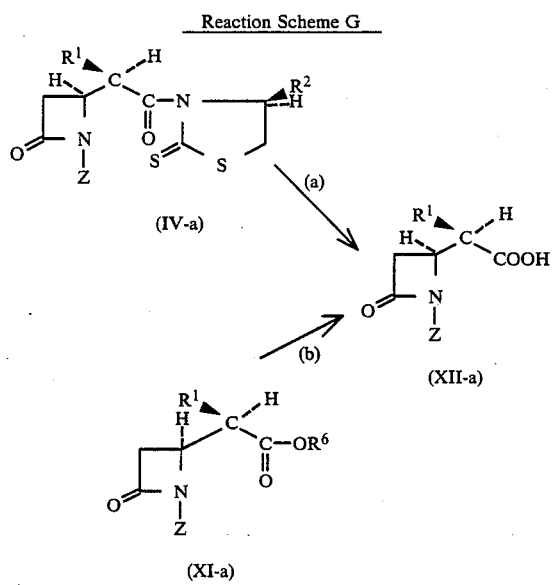

(In the formulae, $R^1$, $R^2$, $R^6$ and Z are as defined above.)

The direct hydrolysis (a) is carried out by treating a solution of the compound of formula (VI-a) in tetrahydrofuran, dioxane, etc. with an aqeous solution of 1 to 1.2 equivalents of lithium hydroxide, sodium hydroxide, potassium hydroxide, etc. at a reaction temperature of about 0° to about 25° C. for about 10 minutes to about 3 hours. Removing of the ester residue (b) can be carried out by a customary method such as hydrolysis or hydrogenation. For example, when $R^6$ in formula (XI-a) is a benzyl group, the compound of formula (XI-a) is treated in a solvent (ethers such as tetrahydrofuran and dioxane, alcohols such as methanol, ethanol and isopropanol, and water, either along or in combination) in the presence of a catalyst such as palladium-carbon at a temperature of about 0° to about 50° C. under a hydrogen pressure of 1 to 4 atmospheres for about 0.5 to about 24 hours.

The conversion of this type can be carried out in the same way also with the compound of formula (I-b) corresponding to the compound of formula (I) in which the substituent $R^3$ is substituted.

The optically active 3-unsubstituted 4-substituted azetidin-2-one derivative obtained as above from the compound of formula (VI-a) can then be converted to the optically active 3,4-disubstituted azetidin-2-one derivative represented by formula (I-b) by introducing a substituent stereoselectively into the 3-position of the former. This will be described below by taking up as an example the introduction of a hydroxyl group as a 3-position substituent into the compound of formula (VI-a) [including both the compounds of formulae (XI-a) and (XII-a)].

The reaction is carried out by acetylating the compound of formula (XIII-a) and subjecting the resulting compound of formula (XIV-a) to a reducing reaction, in accordance with the following reaction scheme H.

Reaction Scheme H

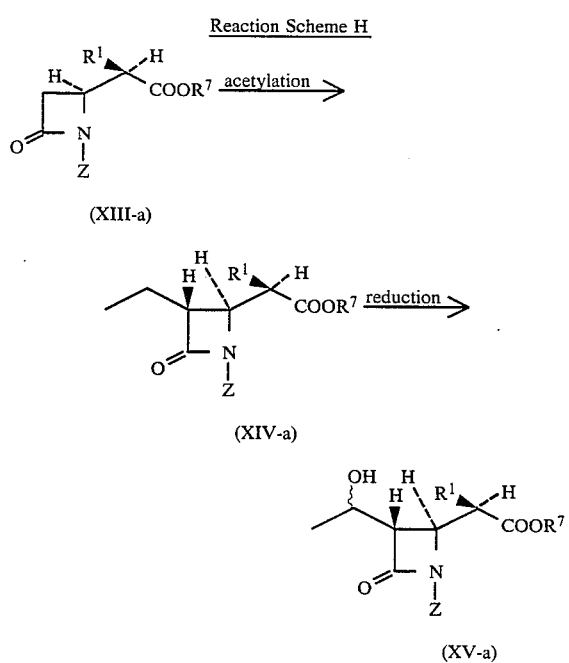

(In the formulae, $R^1$ and $Z$ are as defined, and $R^7$ represents a hydrogen atom or an ester residue.)

The acetylation reaction is carried out by reacting the optically active compound of formula (XIII-a) with an acetylating agent such as N-acetylimidazole, N-acetylpyrazole or N-acetylbenzotriazole in the presence of a base. The amount of the acetylating agent used is about 1 to 4 moles, preferably about 2 to 3 moles, per mole of the compound of formula (XIII-a). Examples of the base are methyllithium, butyllithium, sec-butyllithium, phenyllithium, lithium diisopropylamide or lithium hexamethyl enedisilazane. Lithium diisopropylamide is especially preferred. The amount of the base used is usually about 1 to 5 moles, preferably about 2 to 4 moles, per mole of the compound of formula (XIII-a). This reaction is generally carried out in a solvent such as diethyl ether, tetrahydrofuran, dioxane or dimethoxyethane. The reaction temperature varies depending upon the type of the base and solvent used, but the suitable reaction temperature is generally about −100° to about 300° C., preferably about −80° to about 25 ° C. The reaction time is generally about 5 minutes to about 1 hour. As a result, a trans-isomer of the compound of formula (XIV-a) is obtained stereoselectively as a main product.

By subjecting this product to a reducing reaction, a compound of formula (XV-a) can be produced. Suitable reducing agents for the reaction include, for example, sodium borohydride, lithium tri-sec-butylborohydride, sodium tri-sec-butylborohydride, potasium tri-sec-butylborohydride, trimethylaminoborane and diisopropylaminoborane. The reducing reaction is carried out generally in a solvent (for example, ethers such as diethyl ether, dimethoxyethoxyethane, tetrahydrofuran and dioxane, alcohols such as methanol, ethanol and isopropanol, and water, eitherr alone or in combination) using about 1 to 6 moles, per mole of the compound of formula (XIV-a), of a reducing agent. The suitable reaction temperature is generally about −100° to about 50° C., preferably about −80° to about 30° C. The reaction time varies depending upon the reducing agent, the solvent and the reaction temperature. Generally, it is about 0.5 to 5 hours, preferably about 0.5 to 2 hours.

When it is desired to produce a beta-hydroxy derivative of the following formula (XV-a)′

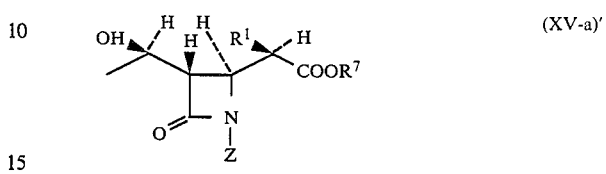

wherein $R^1$, $R^7$ and $Z$ are as defined above, by the stereoselective reduction of the compound of formula (XIV-a) in the above reducing reaction, the use of potassium tri-sec-butylborohydride and diisopropylaminoborane is especially preferred as the reducing agent. Reduction with diisopropylaminoborane is more preferably carried out in the presence of magnesium trifluoroacetate.

The compound of formula (XIV-a) can be produced by reacting the compound of formula (XIII-a) with acetaldehyde in the presence of a base such as lithium diisopropylamide to form the compound of formula (XVI-a), and then oxidizing this compound (XVI-ae with an oxidizing agent such as chromic anhydride, potassium bichromate, pyridinium dichromate, trifluoroacetic acid/dimethylsulfoxice/triethylamine, or acetic anhydride/dimethylsulfoxide, in accordance with the following reaction scheme I.

Reaction scheme I

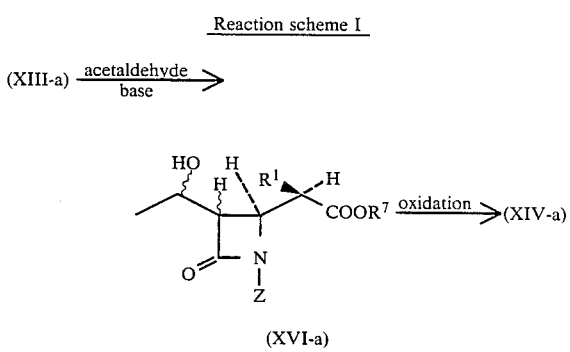

(In the formulae, $R^1$, $R^7$ and $Z$ are as defined above.)

The resulting compound of formula (XV-a) or (XV-a)′ can be converted to thienamycin or 1β-methyl-carbapenem-series antibiotics by methods known per se.

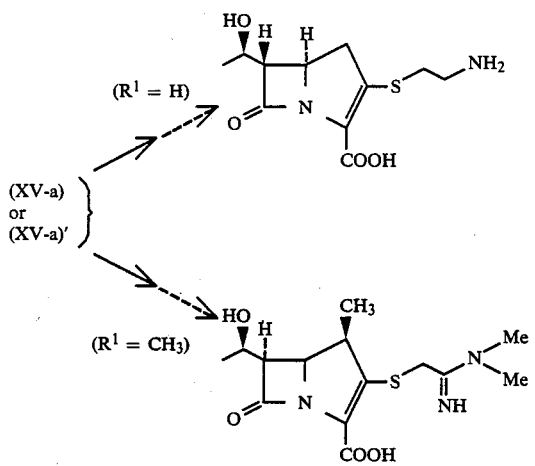

The following examples illustrate the present invention more specifically.

EXAMPLE 1

4S-[(4S-ethyl-1,3-thiazolidine-2-thion-3-yl)-carbonylmethyl]azetidin-2-one:

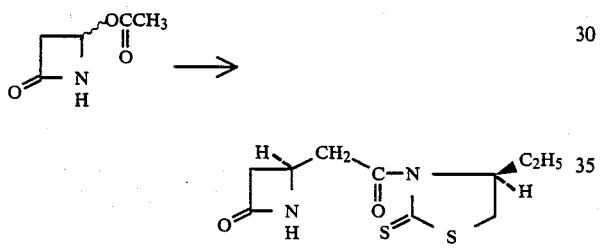

A solution of tin (II) triflate (5.6 g; 13.4 millimoles) in anhydrous tetrahydrofuran (20 ml) was cooled to −50° to −40° C., and in an atmosphere of argon, a solution of N-ethylpiperidine (2.22 ml; 16.1 millimoles) and 3-acetyl-4S-ethyl-1,3-thiazolidine-2-thione (1.78 g; 9.41 millimoles) in anhydrous tetrahydrofuran (10 ml) was added. The mixture was stirred at the above temperature for 4 hours. A solution of 4-acetoxy-2-azetidinone (867 mg; 6.7 millimoles) in anhydrous tetrahydrofuran (10 ml) was added to the mixture, and the resulting mixture was stirred for 1 hour at 0° C.

0.1M phosphate buffer (pH 7.0; 20 ml) and diethyl ether (200 ml) were added to the reaction mixture, and the insoluble materials were separated by filtration with Celite. The ethereal layer was dried over anhydrous sodium sulfate, and the solvent was evaporated under reduced pressure. The residue was purified by silica gel column chromatography (eluent:chloroform/ethyl acetate=3/1) to give the captioned compound (1.3 g, yield 75.0%) as a yellow oil.

$[\alpha]_D^{20}$: +261.9° (c 1.03, CHCl$_3$)

IR(film): 1740, 1680 cm$^{-1}$ $^1$H-NMR($\delta$ppm, CDCl$_3$):1.03 (3H, t, J=8.0 Hz), 2.86 (2H, m), 2.60–3.70 (6H, m), 4.00 (1H, m), 5.16 (1H, m), 6.10 (1H, brs).

EXAMPLE 2

4S-[1R-(4S-ethyl-1,3-thiazolidine-2-thione-3-yl)carbonylethyl]azetidin-2-one:

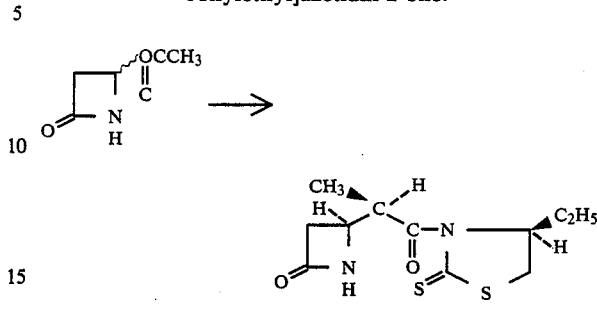

Example 1 was repeated except that 3-propionyl-4S-ethyl-1,3-thiazolidine-2-thione was used instead of 3-acetyl-4S-ethyl-1,3-thiazolidine-2-thione. The captioned compound (yield 81.5%) was obtained as yellow needles.

Melting point: 121°–122° C.

$[\alpha]_D^{25}$: +266.7° (c=0.2, CHCl$_3$)

IR (CHCl$_3$): 1760 cm$^{-1}$ $^1$H-NMR($\delta$ppm, CDCl$_3$): 1.01 (3H, t, J=7.4 Hz), 1.24 (3H, d, J=6.6 Hz), 1.66–2.10 (2H, m), 2.73–3.20 (3H, m), 3.40–3.65 (1H, m), 3.90–4.05 (1H, m), 4.85–5.30 (2H, m) 6.20 (1H, brs).

The compounds given in Table 1 were synthesized in accordance with the methods described in Examples 1 and 2.

EXAMPLE 3

1-t-Butyldimethylsilyl-4R-[(4S-ethyl-1,3-thiazolidine-2-thion-3-yl)carbonylmethyl]azetidin-2-one:

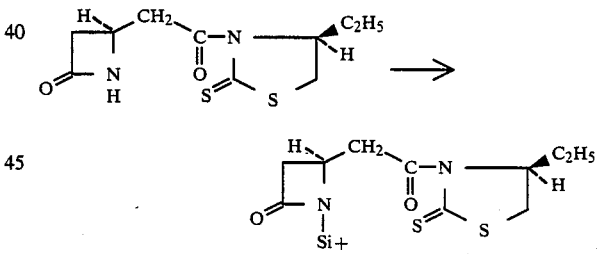

A solution of 4S-[(4S-ethyl-1,3-thiazolidine-2-thion-3-yl)carbonylmethyl]azetidin-2-one (461 mg; 1.79 millimoles) in anhydrous dimethylformamide (10 ml) was cooled with ice, and in an atmosphere of nitrogen gas, t-butyldimethylchlorosilane (539 mg; 3.58 millimoles) and triethylamine (1 ml; 7.16 millimoles) were added. The mixture was stirred under ice cooling for 30 minutes. A benzene/n-hexane (1/1) mixture (150 ml) and water (80 ml) were added to the reaction mixture. The organic layer was dried over anhydrous sodium sulfate, and the solvents were evaporated under reduced pressure. The residue was purified by silica gel column chromatography (eluent:chloroform/ethyl acetate=9/1) to give the captioned compound (650 mg, yield 97.6%) as a yellow oil.

$^1$H-NMR($\delta$ppm, CDCl$_3$): 0.24 (6H, s), 0.96 (9H, s), 1.03 (3H, t, J=8.0 Hz), 1.85 (2H, m), 2.60–4.00 (7H, m), 5.15 (1H, m).

EXAMPLE 4

1-t-Butyldimethylsilyl-4S-[1R-(4S-ethyl-1,3-thiazolidine-2-thione-3-yl)carbonylethyl]azetidin-2-one:

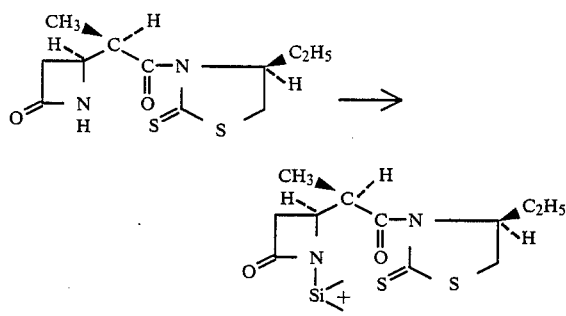

Example 3 was repeated except that 4S-[1R-(4S-ethyl-1,3-thiazolidine-2-thion-3-yl)carbonylethyl]azetidin-2-one was used instead of 4S-[(4S-ethyl-1,3-thiazolidine-2-thion-3-yl)carbonylmethyl]azetidin-2-one. The captioned compound (yield 99.3%) was obtained as yellow crystals.
Melting point:94°–95° C.
$[\alpha]_D^{25}$:+71.9° (c=0.6, CHCl$_3$)
IR(CHCl$_3$):1735, 1705 cm$^{-1}$
$^1$H-NMR($\delta$ppm,CDCl$_3$):0.20 (3H, s), 0.26 (3H, s), 0.95 (9H, s), 1.02 (3H, t, J=7.5 Hz), 1.25 (3H, d, J=7 Hz), 1.72–2.03 (2H, m), 2.95 (1H, dd, J=10 , 1.5 Hz), 3.10–3.20 (2H, m), 3.40–3.80 (2H, m), 4.97–5.30 (2H, m).

EXAMPLE 5

4S-[2S-(1-hydroxy)propyl]azetidin-2-one:

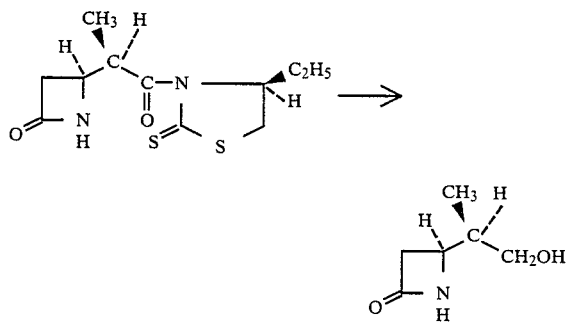

Sodium borohydride (16.8 mg; 0.4 millimole) was dissolved in a tetrahydrofuran/ethanol (1/1) mixture (1 ml), and the solution was cooled to −15° C. A solution of 4S-[1R-(4S-ethyl-1,3-thiazolidine-2-thion-3-yl)carbonylethyl]azetidin-2-one (163.2 mg; 0.6 millimole) in a tetrahydrofuran/ethanol mixture (1 ml) was added to the solution. The mixture was stirred at −15° C. for 45 minutes. The reaction mixture was neutralized with 10% hydrochloric acid and then extracted with ethyl acetate. The extract was dried over anhydrous sodium sulfate, and the solvents were evaporated. The residue was purified by silica gel column chromatography (eluent:ethyl acetate) to give the captioned compound (46.5 mg, yield 60%) as a colorless oil.
IR(neat):1740 cm$^{-1}$
$^1$H-NMR($\delta$ppm, CDCl$_3$):0.96 (3H, d, J=7 Hz), 1.60–2.00 (1H, m), 2.63–2.77 (1H, m), 2.90–3.15 (1H, m), 3.30 (1H, brs), 3.50–3.73 (3H, m), 6.90 (1H, brs).

EXAMPLE 6

(6S)-2,2,5S-Trimethyl-3-oxa-1-azabicyclo[4.2.0]octan-8-one:

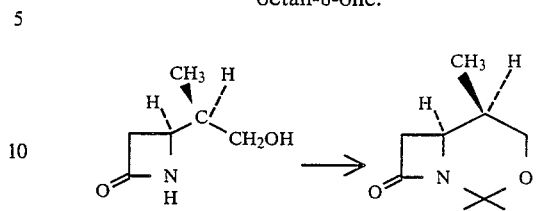

Boron trifluoride etherate (5.1 mg; 0.036 millimole) was added to a solution of 4S-[2S-(1-hydroxy)propyl]azetidin-2-one (46.5 mg; 0.36 millimoles) and 2,2-dimethoxypropane (44.6 mg; 0.43 millimole) in methylene chloride (1 mg), and the solution was stirred at room temperature for 90 minutes. The reaction mixture was washed with a saturated aqueous sodium bicarbonate solution and a saturated aqueous sodium chloride solution, and dried over anhydrous sodium sulfate, and the solvent was evaporated under reduced pressure. The residue was purified by silica gel column chromatography (eluent:n-hexane/ethyl acetate=6/4) to give the captioned compound (47.8 mg, yield 78.5%) as a colorless oil.
$[\alpha]_D^{25}$:+47.1° (C=0.4, CHCl$_3$)
IR(neat):1745 cm$^{-1}$
$^1$H-NMR($\delta$ppm, CDCl$_3$):1.10 (3H, d, J=7.5 Hz), 1.40 (3H, s), 1.72 (3H, s), 1.83–2.05 (1H, m), 2.65–3.05 (2H, m), 3.60 (1H, dd, J=13, 3 Hz), 3.70–3.83 (1H, m), 3.97 (1H, dd, J=13, 2 Hz).

EXAMPLE 7

1-t-Butyldimethylsilyl-4S-benzyloxycarbonylmethylazetidin-2-one:

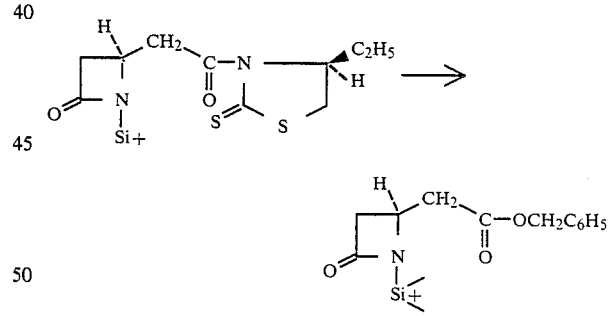

Sodium benzyloxide (476 mg; 3.67 millimoles) was added under ice cooling to a solution of 1-t-butyldimethylsilyl-4R-[(4S-ethyl-1,3-thiazolidine-2-thion-3-y) carbonylmethyl]azetidin-2-one (1.364 mg; 3.67 millimoles) in toluene (10 ml). The mixture was stirred for 1 hour at 0° C. and further for 30 minutes at room temperature. The solvent was evaporated under reduced pressure from the reaction mixture. The residue was purified by silica gel column chromatography (eluent:n-hexane/ethyl acetate=4/1) to give the captioned compound (797 mg, yield 65.3%).
$[\alpha]_D^{20}$:−61.6° (c 1.07, CHCl$_3$)
$^1$H-NMR($\delta$ppm, CDCl$_3$):0.2 (3H, s), 0.23 (3H, s), 0.95 (9H, s), 2.35–3.40 (4H, m), 3.90 (1H, m), 5.12 (2H, s), 7.34 (5H, s).

EXAMPLE 8

1-t-Butyldimethylsilyl-4S-(1R-benzyloxycarbonylethyl)azetidin-2-one:

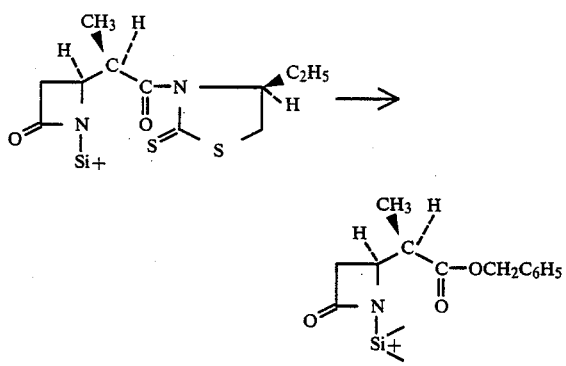

Example 7 was repeated except that 1-t-bytyldimethylsilyl-4S-[1R-(4S-ethyl-1,3-thiazolidine-2-thion-3-yl)carbonylethyl]azetidin-2-one was used as the starting material. The captioned compound (yield 58.8%) was obtained as a slightly yellow oil.

IR(neat):1740 cm$^{-1}$ $^1$H-NMR(δppm, CDCl$_3$):0.15 (3H, s), 0.19 (3H, s), 0.93 (9H, s), 1.17 (3H, d, J=7 Hz), 2.70-3.12 (3H, m), 3.63-3.80 (1H, m), 5.03 (1h, d, J=12 Hz), 5.17 (1H, d, J=12 Hz), 7.35 (5H, s).

EXAMPLE 9

4R-Benzyloxycarbonylmethylcarbonylmethylazetidin-2-one:

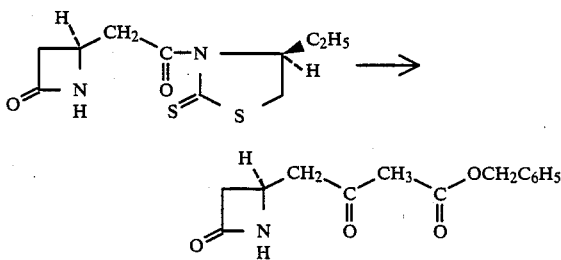

A solution of diisopropylamine (0.099 ml; 0.71 millimole) in anhydrous tetrahydrofuran (1.4 ml) was cooled to 0° C., and a 1.5M hexane solution of n-butyllithium (0.47 ml; 0.71 millimole) was added. The mixture was stirred at 0° C. for 15 minutes, and then cooled to −78° C. A solution of benzyl acetate (107 mg; 0.71 millimoles) in tetrahydrofuran (0.5 ml) was added, and the mixture was stirred at the above temperature for 1 hour. A solution of 4S-[(4S-ethyl-1,3-thiazolidine-2-thion-3-yl)carbonylmethyl]azetidin-2-one (175 mg; 0.68 millimoles) in tetrahydrofuran (0.5 ml) was added. The mixture was stirred at the above temperature for 5 minutes, and a saturated aqueous ammonium chloride solution was added. The mixture was extracted with ethyl acetate. The extract was dried over anhydrous sodium sulfate, and the solvent was evaporated under reduced pressure. The residue was purified by silica gel column chromatography (eluent:chloroform/acetone=3/1) to give the captioned compound (54 mg, yield 30.6%) as a slightly yellow oil.

[α]$_D^{20}$:+43.2° (c=0.86, benzene)
IR(CHCl$_3$):1750 cm$^{-1}$ $^1$H-NMR(δppm, CDCl$_3$):2.54-2.58 (1H, m), 2.76 (1H, dd, J=18.1, 9.3 Hz), 2.98 (1H, dd, J=18.1, 4.4 Hz), 3.10-3.15 (1H, m), 3.50 (2H, s), 3.90-3.95 (1H, m), 5.18 (2H, s), 6.09 (1H, brs), 7.33-7.40 (5H, m).

EXAMPLE 10

1-t-Butyldimethylsilyl-4S-carboxymethylazetidin-2-one:

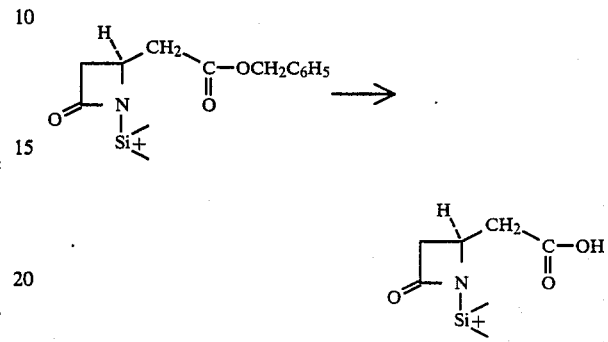

A solutin of 1-t-butyldimethylsilyl-4S-benzyloxycarbonylmethylazetidin-2-one (297 mg; 0.89 millimole) in methanol (5 ml) was subjected to catalytic hydrogenation at room temperature for 18 hours in the presence of 5% palladium-carbon (60 mg). The reaction mixture was filtered, and the solvent was evaporated under reduced pressure to give the captioned compound (187 mg, yield 86.6%) as a white solid.

IR(KBr):1725, 1680 cm$^{-1}$ $^1$H-NMR(δppm, CDCl$_3$):0.23 (3H, s), 0.26 (3H, s), 0.96 (9H, s), 2.30-3.43 (4H, m), 3.90 (1H, m), 8.20 (1H, brs).

EXAMPLE 11

1-t-Butyldimethylsilyl-4S-(1R-carboxyethyl)azetidin-2-one:

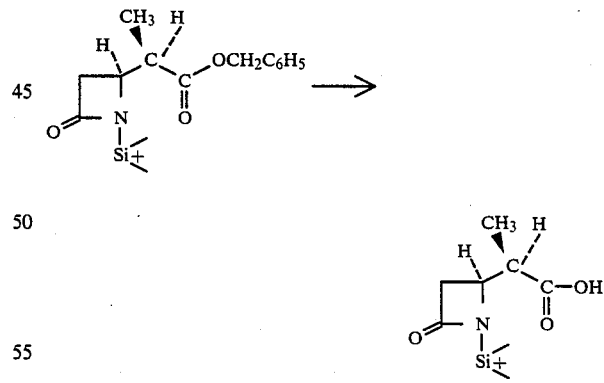

Example 10 was repeated except that 1-t-butyldimethylsilyl-4S-(1R-benzyloxycarbonylethyl)azetidin-2-one was used as the starting material. The captioned compound (yield 99.3%) was obtained as colorless needles.

Melting point: 128°-129° C.
[α]$_D^{26}$: −66.7° (c 0.6, CHCl$_3$)
IR(CHCl$_3$): 1730 cm$^{-1}$ $^1$H-NMR (δppm, CDCl$_3$): 0.22 (3H, s), 0.27 (3H, s), 0.97 (9H, s), 1.18 (3H, d, J=7 Hz), 2.81-3.17 (3H, m), 3.60-3.81 (1H, m).

EXAMPLE 12

1-t-Butyldimethylsilyl-4S-(1R-carboxyethyl)-azetidin-2-one:

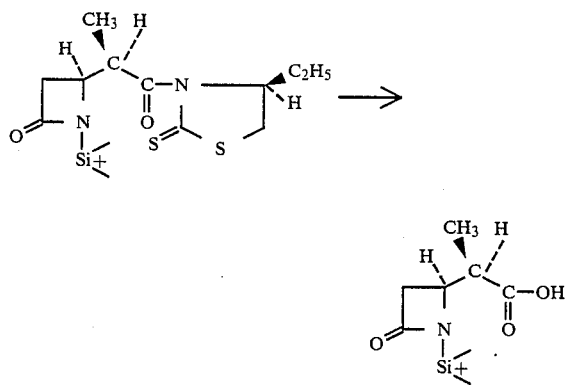

A solution of lithium hydroxide (46 mg; 1.1 millimoles) in water (2 ml) was added under ice cooling to a solution of 1-t-butyldimethylsilyl-4S-[1R-(4S-ethyl-1,3-thiazolidine-2-thion-3-yl)carbonylethyl]azetidin-2-one (386 mg; 1 millimole) in tetrahydrofuran (5 ml), and the mixture was stirred for 30 minutes under ice cooling. The reaction mixture was neutralized with potassium hydrogen sulfate, and then extracted with chloroform. The extract was dried over anhydrous sodium sulfate, and the solvent was evaporated under reduced pressure. The residue was purified by silica gel column chromatography (eluent: chloroform/acetone=9/1) to give the captioned compound (107 mg, yield 41.6%).

The property values of the product agree with those of the product obtained in Example 11.

EXAMPLE 13

1-t-Butyldimethylsilyl-3S-acetyl-4R-(1R-carboxyethyl-)azetidin-2-one:

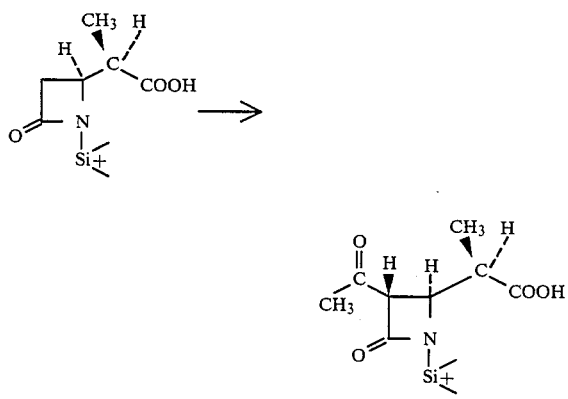

A 1.56M n-hexane solution of n-butyllithium (4.2 ml) was added at 0° to −5° C. to a solution of diisopropylamine (669 mg; 6.6 millimoles) in tetrahydrofuran (10 ml). The mixture was stirred at this temperature for 1.5 minutes and then cooled to −40° C. A solution of 1-t-butyldimethylsilyl-4S-(1R)-carboxyethyl)azetidin-2-one (540 mg; 2.1 milimoles) in tetrahydrofuran (10 ml) was added. The solution was stirred at −40° C. for 15 minutes and then cooled to −78° C. The solution was added dropwise to a solution of acetylimidazole (484 mg; 4.4 millimoles) in tetrahydrofuran (15 ml) cooled at −78° C. After the addition, the mixture was stirred at room temperature for 15 minutes. A 10% aqueous citric acid solution was added to the reaction mixture, and the mixture was extracted with ethyl acetate. The extract was washed with a saturated sodium chloride solution and dried over anhydrous sodium sulfate, and the solvent was evaporated under reduced pressure. The residue was purified by silica gel column chromatography (eluent: chloroform/acetone=9/1) to give the captioned compound (521 mg, yield 83%) as a slightly yellow oil.

IR(neat): 1740, 1710 cm$^{-1}$ $^1$H-NMS($\delta$ppm, CDCl$_3$): 0.23 (3H, s), 0.28 (3H, s), 0.93 (9H, s), 1.18 (3H, d, J=7 Hz), 2.32 (3H, s), 2.92-3.14 (1H, m), 4.11 (1H, dd, J=3, 5 Hz), 4.61 (1H, d, J=3 Hz), 8.53 (1H, brs).

EXAMPLE 14

1-t-Butyldimethylsilyl-3S-(1R-hydroxyethyl)-4S-(1R-carboxyethyl)azetidin-2-one:

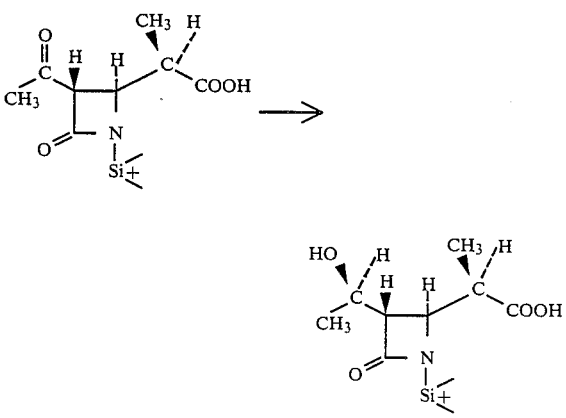

A solution of 1-t-butyldimethylsilyl-3S-acetyl-4R-(1R-carboxyethyl)azetidin-2-one (437 mg; 1.46 millimoles) in diethyl ether (15 ml) was cooled to −78° C., and a 1M diethyl ether solution (7.3 ml) of magnesium trifluoroacetate was added. The mixture was stirred at −78° C. for 20 minutes. A diisopropylamine-borane complex (0.4 ml) was added, and the mixture was stirred at the above temperature for 1 hours. A 10% aqueous citric acid solution was added to the reaction mixture, and the entire mixture was extracted with ethyl acetate. The extract was washed with a 10% aqueous citric acid solution and a saturated aqueous sodium chloride solution, and dried over anhydrous sodium sulfate. The solvent was evaporated under reduced pressure, and the residue was purified by silica gel column chromatography (eluent: chloroform/acetone=7/3) to give the captioned compound (314 mg, yield 71%) as colorless crystals.

Melting point: 130°-132° C.

$[\alpha]_D^{26}$: −54.6° (c 0.5, CHCl$_3$)

IR(CHCl$_3$): 1730 cm$^{-1}$ $^1$H-NMR($\delta$ppm, CDCl$_3$): 0.23 (3H, s), 0.28 (3H, s), 0.96 (9H, s), 1.22 (3H, d, J=6 Hz), 1.30 (3H, d, J=6 Hz), 2.82-3.10 (1H, m), 3.43 (1H, dd, J=2.5 Hz), 3.76 (1H, dd, J=2, 5 Hz), 4.03-4.30 (1H, m), 6.65 (2H, brs).

EXAMPLE 15

3S-(1R-tert-Butyldimethylsilyloxyethyl)-4R-[(4S-ethyl-1,3-thiazolidine-2-thion-3-yl)carbonylmethyl]azetidin-2-one:

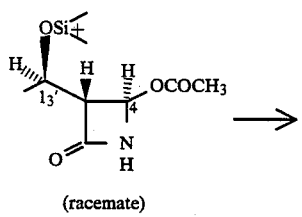

(racemate)

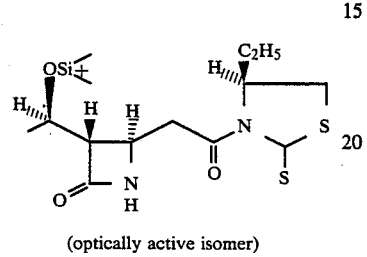

(optically active isomer)

A solution of n-ethylpiperidine (0.74 ml; 5.45 millimoles) and 3-acetyl-4S-ethyl-1,3-thiazolidine-2-thione (454 mg, 2.4 mmoles) in anhydrous tetrahydrofuran (6 ml) was added to a solution of tin (II) triflate (1.89 g; 4.54 millimoles) in anhydrous tetrahydrofuran (8 ml) cooled at −50° to −40° C., and the mixture was stirred at the above temperature for 4 hours. A solution of 3-(1-tert-butyldimethylsiloxyethyl)-4-acetoxyazetidin-2-one [a racemate of (1',3)threo-(3,4)trans] (690 mg; 2.4 millimoles) in anhydrous tetrahydrofuran (6 ml) was added, and the mixture was stirred at 0° C. for 50 minutes. To the reaction mixture were added 0.1M phosphate buffer (pH 7.0; 3 ml) and diethyl ether (50 ml), and the insoluble materials were separated by filtration with Celite. The filtrate was dried over anhydrous sodium sulfate, and then the solvent was evaporated under reduced pressure. The resisdue was subjected to silica gel column chromatography (eluent: chloroform/ethyl acetate=20/1) to obtain the captioned compound (420 mg, yield 42%; yellow solid) as a second eluate.

IR(neat): 1750, 1695 cm$^{-1}$
$^1$H-NMR(δppm, CDCl$_3$): 0.08 (6H, s), 0.87 (9H, s), 1.02 (3H, t, J=8 Hz), 1.23 (3H, d, J=6 Hz), 1.71–2.06 (2H, m), 2.81–3.32 (3H, m), 3.46–3.68 (2H, m), 3.92–4.35 (2H, m), 5.02–5.25 (1H, m), 6.05 (1H, brs).
Rf: 0.38 (chloroform/ethyl acetate=4/1)

The following compounds were obtained as a first and a third eluate.

First eluate (yellow oil, 195 mg, 19.5%)

3R-(1S-tert-Butyldimethylsilyloxyethyl)-4S-[(4S-ethyl-1,3-thiazolidine-2-thion-3-yl)carbonylmethyl]azetidin-2-one.

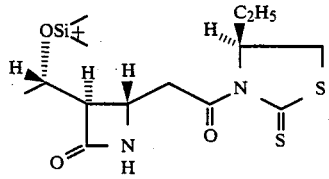

IR(neat): 1750, 1695 cm$^{-1}$ $^1$H-NMR(δppm, CDCl$_3$): 0.06 (6H, s), 0.87 (9H, s), 1.02 (3H, t, J=8 Hz), 1.21 (3H, d, J=6 Hz), 1.66–2.20 (2H, m), 2.80–3.26 (3H, m), 3.46–3.77 (2H, m), 3.86–4.07 (1H, m), 4.13–4.33 (1H, m), 5.02–5.26 (1H, m), 6.25 (1H, brs).
Rf: 0.50 (chloroform/ethyl acetate=4/1)

Third eluate (yellow oil, 90 mg, 9.0%)

3R-(1S-tert-Butyldimethylsilyloxyethyl)-4R-[(4S-ethyl-1,3-thiazolidine-2-thion-3-yl)carbonylmethyl]azetidin-2-one.

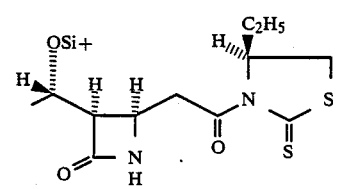

IR(neat): 1755, 1685 cm$^{-1}$
$^1$H-NMR(δppm, CDCl$_3$): 0.09 (6H, s), 0.86 (9H, s), 1.02 (3H, t, J=8 Hz), 1.32 (3H, d, J=6 Hz), 1.70–2.02 (2H, m), 3.46–4.42 (4H, m), 5.05–5.25 (1H, m), 6.06 (1H, brs).
Rf: 0.30 (chloroform/ethyl acetate=4/1)

EXAMPLE 16

3S-(1R-tert-Butyldimethylsilyloxyethyl)-4R-[1R-45-isopropyl-1,3-thiazolidine-2-thion-3-yl)carbonylethyl]azetidin-2-one:

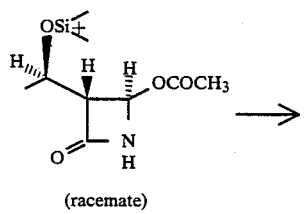

(racemate)

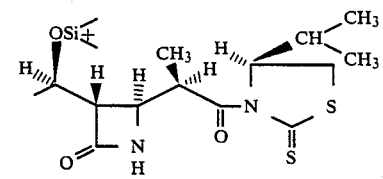

(optically active isomer)

Example 15 was repeated except that 3-propionyl-4S-isopropyl-1,3-thiazolidine-2-thione was used instead of 3-acetyl-4S-ethyl-1,3-thiazoline-2-thione. By column chromatography, the captioned compound (yellow crystals, yield 32.3%) was obtained as a main eluate.
Melting point: 126°–127° C.
IR(CHCl$_3$): 1760, 1695 cm$^{-1}$
$^1$H-NMR(δppm, CDCl$_3$): 0.08 (6H, s), 0.87 (9H, s), 0.96 (3H, d, J=7 Hz), 1.04 (3H, d, J=7 Hz), 1.19 (3H, d, J=7 Hz), 1.23 (3H, d, J=7 Hz), 2.14–2.42 (1H, m), 2.94–3.12 (2H, m), 3.47 (1H, dd, J=11 Hz, 8 Hz), 3.87–4.30 (2H, m), 4.95–5.24 (2H, m), 6.17 (1H, brs).

EXAMPLE 17

3S-(1S-tert-Butyldimethylsilyloxyethyl)-4R-[(4S-ethyl-1,3-thiazolidine-2-thion-3-yl)carbonylmethyl]azetidin-2-one:

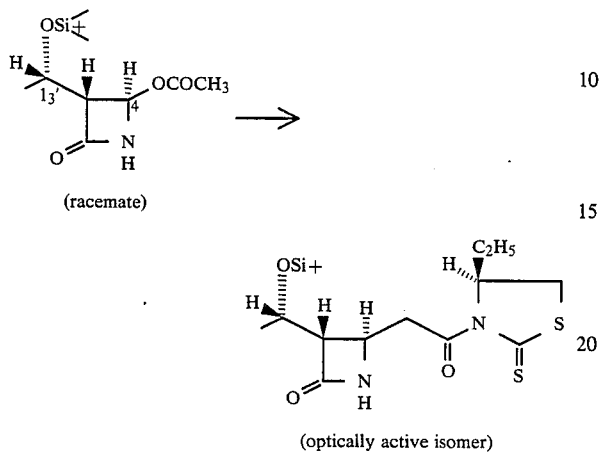

A solution of N-ethylpiperidine (0.83 ml; 6 millimoles) and 3-acetyl-4S-ethyl-1,3-thiazolidine-2-thione (510 mg; 2.7 millimoles) in anhydrous tetrahydrofuran (6 ml) was added to a solution of tin (II) triflate (2.09 g; 5 millimoles) in anhydrous tetrahydrofuran (8 ml) cooled at −50° to −40° C., and the mixture was stirred at the above temperature for 3.5 hours. To the solution was then added a solution of 3-(1-tert-butyldimethyl-siloxy)ethyl-4-acetoxyazetidin-2-one [a racemate of (1′,3)erythro-(3,4)trans] (775 mg; 2.7 millimoles) in anhydrous tetrahydrofuran (6 ml), and the mixture was stirred at 0° C. for 50 minutes. To the reaction mixture were added 0.1M phosphate buffer (pH 7.0; 5 ml) and diethyl ether (50 ml), and the insoluble materials were separated by filtration with Celite. The filtrate was dried over anhydrous sodium sulfate, and the solvent was evaporated under reduced pressure. The residue was subjected to silica gel column chromatography (eluent: chloroform/ethyl acetate=15/1) to give the captioned compound (yellow oil, 510 mg, 45.4%) as a second eluate.

IR(neat): 1750, 1680 cm$^{-1}$ $^1$H-NMR(δppm, CDCl$_3$): 0.08 (6H, s), 0.89 (9H, s), 1.03 (3H, t, J=8 Hz), 1.32 (3H, d, J=6 Hz), 1.66–2.09 (2H, m), 2.86–3.73 (5H, m), 3.82–4.37 (2H, m), 5.01–5.27 (1H, m), 6.12 (1H, brs).

Rf: 0.55 (chloroform/ethyl acetate=4/1)

The following compounds were obtained as a first and a third eluate.

First eluate (yellow solid, 320 mg, 28.5%)

3R-(1R-tert-Butyldimethylsilyloxyethyl)-4S-[(4S-ethyl-1,3-thiazolidine-2-thion-3-yl)carbonylmethyl]azetidin-2-one.

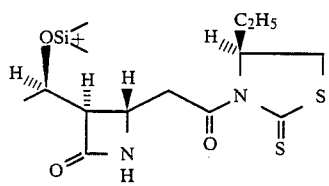

IR(neat): 1755, 1690 cm$^{-1}$ $^1$H-NMR(δppm, CDCl$_3$): 0.07 (6H, s), 0.88 (9H, s), 1.02 (3H, t, J=8 Hz), 1.31 (3H, d, J=6 Hz), 1.63–2.09 (2H, m), 2.86–3.06 (3H, m), 3.45–3.72 (2H, m), 3.76–4.35 (2H, m), 5.02–5.33 (1H, m), 6.05 (1H, brs).

Rf: 0.60 (chloroform/ethyl acetate=4/1)

Third eluate (yellow solid, 56 mg, 5.0%)

3R-(1R-tert-butyldimethylsilyloxyethyl)-4R-[(4S-ethyl-1,3-thiazolidin-2-on-3-yl)carbonylmethyl]azetidin-2-one.

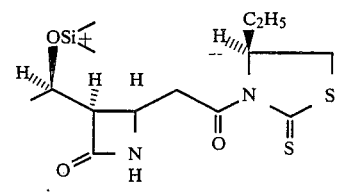

IR(neat): 1750, 1690 cm$^{-1}$ $^1$H-NMR (δppm, CDCl$_3$): 0.1 (6H, s), 0.88 (9H, s), 1.03 (3H, t, J=8 Hz), 1.38 (3H, d, J=6 Hz), 1.69–2.08 (2H, m), 2.86–3.04 (2H, m), 3.22–3.68 (3H, m), 3.92–4.38 (2H, m), 5.00–3.31 (1H, m), 5.96 (1H, brs).

Rf: 0.40 (chloroform/ethyl acetate=4/1)

EXAMPLE 18

4S-[R-(4S-isopropyl-1,3-thiazolidine-2-thion-3-ylcarbonyl)methoxymethyl]azetidin-2-one:

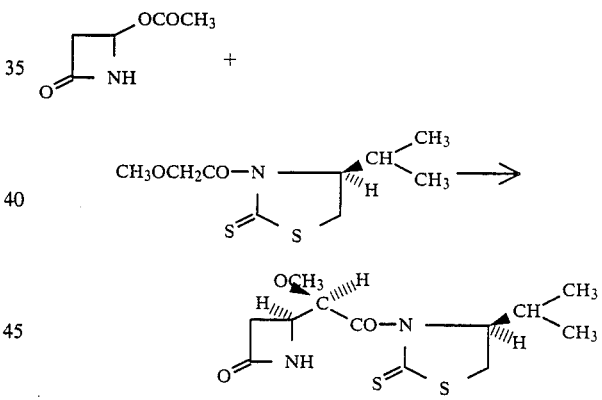

A solution of 3-methoxyacetyl-4(S)-isopropyl-1,3-thiazolidine-2-thione (254 mg; 1.09 millimoles) in tetrahydrofuran (1.2 ml) was added to a solution of tin (II) triflate (584.6 mg; 1.40 millimoles) in tetrahydrofuran (2.3 ml) cooled at −78° C., and then N-ethylpiperidine (0.2 ml; 1.47 millimoles) was added dropwise. The mixture was stirred at this temperature for 30 minutes to form an enol. The ice bath was removed, and immediately then, a solution of 4-acetoxyazetidin-2-one (100.6 mg; 0.78 millimoles) in tetrahydrofuran (1.2 ml) was added. The mixture was stirred at 0° C. for 30 minutes. To the reaction mixture was added 0.1M phosphate buffer, and the mixture was extracted with diethyl ether. The organic layer was washed with 10% hydrochloric acid, water and a saturated aqueous sodium chloride solution, and dried over anhydrous sodium sulfate. The solvent was evaporated under reduced pressure, and the residue was purified by silica gel column chromatography (eluent: chloroform/acetone=95/5) to give the captioned compound (128.6 mg; yield 54.6%) as yellow needles (recrystallized from ethyl acetate).
m.p.: 150°-151° C.,
[α]$_D^{25}$: +516.1° (c=0.22, CHCl$_3$), IR(CHCl$_3$): 1760, 1695 cm$^{-1}$
NMR(CDCl$_3$)δ: 0.97 (3H, d, J=7.0 Hz), 1.06 (3H, d, J=7.0 Hz), 2.05-2.48 (1H, m), 2.83-3.28 (3H, m), 3.38 (3H, s), 3.62 (1H, dd, J=11.7, 7.9 Hz), 4.03-4.18 (1H, m), 5.26 (1H, t, J=7.9 Hz), 6.01 (1H, brs), 6.01 (1H, brs), 6.08 (1H, d, J=4.6 Hz).

EXAMPLE 19

4S-[R-(4S-Ethyl-1,3-thiazolidine-2-thion-3-ylcarbonyl)-methoxymethyl]azetidin-2-one:

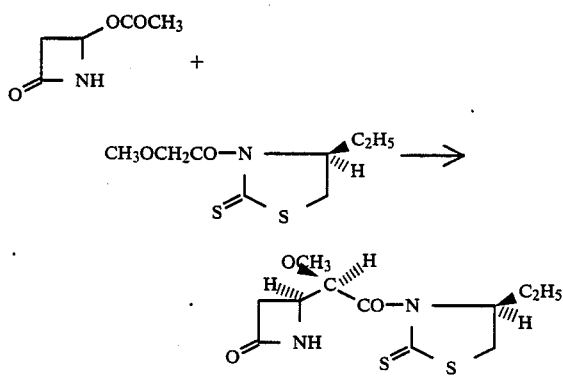

By operating as in Example 18, the captioned compound was obtained in a yield of 61.3%.
IR(CHCl$_3$): 1760, 1695 cm$^{-1}$
NMR(CDCl$_3$)δ: 1.01 (3H, t, J=7.4 Hz), 1.72-2.11 (2H, m), 3.00-3.22 (3H, m), 3.40 (3H, s), 3.68 (1H, dd, J=11.7, 7.3 Hz), 4.02-4.18 (1H, m), 5.12-5.35 (1H, m), 6.02 (1H, d, J=4.8 Hz), 6.42 (1H, brs).

EXAMPLE 20

4S-[R-(4S-isopropyl-1,3-thiazolidine-2-thion-3-ylcarbonyl)methylthiomethyl]azetidin-2-one:

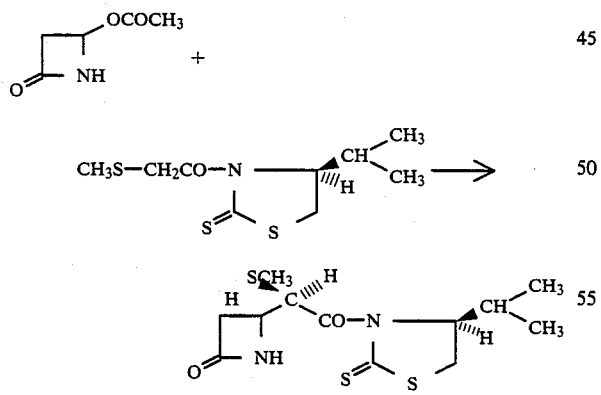

By operating as in Example 18, the captioned compound was obtained in a yield of 72.4% as yellow needles.
m.p.: 147°-148° C.
[α]$_D^{25}$: +247.6° (c 0.25, CHCl$_3$)
IR(CHCl$_3$): 1765, 1680 cm$^{-1}$,
NMR(CDCl$_3$)δ: 0.99 (3H, d, J=7.0 Hz), 1.08(3H, d, J=7.0 Hz), 2.13 (3H, s), 2.20-2.57 (1H, m), 2.83-3.37 (3H, m), 3.93 (1H, dd, J=11.4, 7.4 Hz), 4.03-4.24 (1H, m), 5.00 (1H, t, J=7.4 Hz), 5.90 (1H, d, J=7.6 Hz), 6.16 (1H, brs).

EXAMPLE 21

4S-[R-(4S-ethyl-1,3-thiazolidine-2-thion-3-ylcarbonyl)-methylthiomethyl]azetidin-2-one:

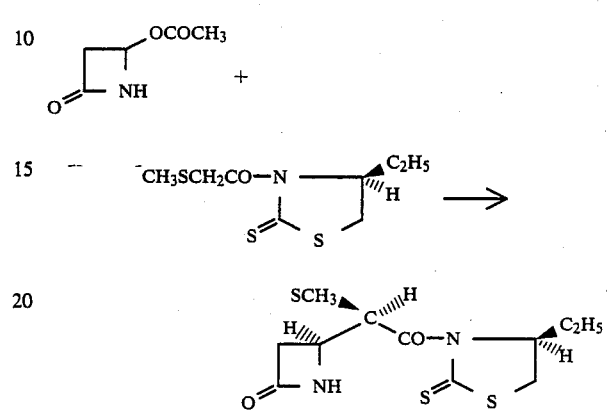

By operating as in Example 18, the captioned compound was obtained in a yield of 75%.
IR(CHCl$_3$): 1765, 1685 cm$^{-1}$
NMR(CDCl$_3$)δ: 1.02 (3H, t, J=7.4 Hz), 1.68-2.09 (2H, m), 2.13 (3H, s), 2.83-3.26 (3H, m), 3.60 (1H, dd, J=11.4, 7.2 Hz), 4.06-4.22 (1H, m), 4.85-5.12 (1H, m), 5.88 (1H, d, J=7.6 Hz), 6.21 (1H, brs).

EXAMPLE 22

4S-[R-(4S-isopropyl-1,3-thiazolidine-2-thion-3-ylcarbonyl)benzyloxymethyl]azetidin-2-one:

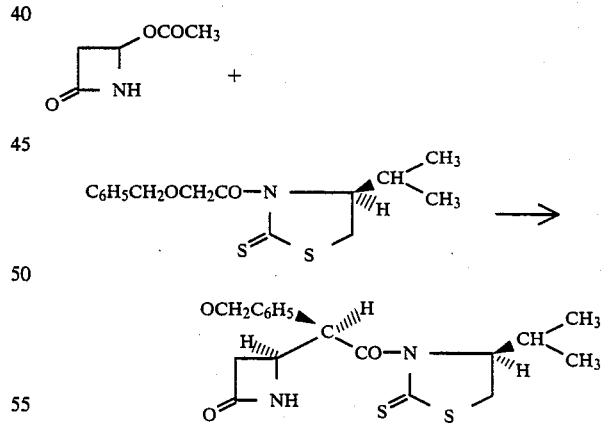

By operating as in Example 18, the captioned compound was obtained in a yield of 79.1%.
m.p.: 105°-120° C.
[α]$_D^{25}$:+407.0° (c 0.29, CHCl$_3$)
IR(CHCl$_3$): 1760, 1690 cm$^{-1}$
NMR(CDCl$_3$)δ: 0.90 (3H, d, J=6.9 Hz), 0.99 (3H, d, J=6.9 Hz), 2.01-2.37 (1H, m), 2.88-3.37 (4H, m), 3.95-4.18 (1H, m), 4.57 (2H, dd, J=11.9, 16.5 Hz), 4.77-4.98 (1H, m), 6.02 (1H, brs), 6.21 (1H, d, J=8.4 Hz), 7.34 (5H, s).

EXAMPLE 23

4S-[R-(4S-isopropyl-1,3-thiazolidine-2-thion-3-ylcarbonyl)benzylthiomethyl]azetidin-2-one:

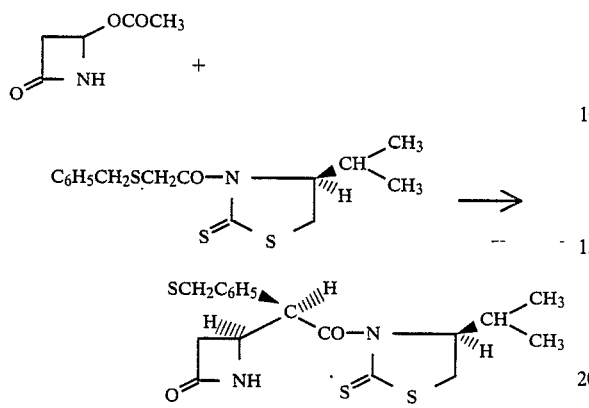

By operating as in Example 18, the captioned compound was obtained in a yield of 84.3%.

$[\alpha]_D^{25}$: +252.8° (c 0.36, CHCl$_3$)

IR(CHCl$_3$): 1760, 1680 cm$^{-1}$

NMR(CDCl$_3$)δ: 0.92 (3H, d, J=6.9 Hz), 1.01 (3H, d, J=6.9 Hz), 2.10–2.50 (1H, m), 2.85–3.07 (3H, m), 3.27 (1H, dd, J=7.4, 11.5 Hz), 3.81 (2H, s), 3.97–4.15 (1H, m), 4.62–4.79 (1H, m), 5.89 (1H, d, J=6.3 Hz), 6.00 (1H, brs), 7.31 (5H, s).

EXAMPLE 24

4S-[R-(4S-isopropyl-1,3-thiazolidine-2-thion-3-ylcarbonyl)benzyloxycarbonylaminomethyl]azetidin-2-one:

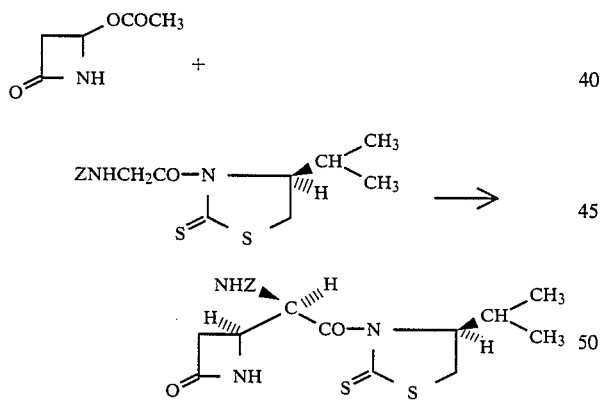

(Z = C$_6$H$_5$CH$_2$OCO—)

An enol formed from 3-benzyloxycarbonylglycyl-4S-isopropyl-1,3-thiazolidine-2-thione was reacted with 4-acetoxyazetidin-2-one at 0° C. for 10 minutes. Otherwise, by operating as in Example 18, the captioned compound was obtained in a yield of 52.1%.

$[\alpha]_D^{25}$: +219.7° (c 0.38, CHCl$_3$)

IR(CHCl$_3$): 1765, 1720, 1685 cm$^{-1}$

NMR(CDCl$_3$)δ: 0.93 (3H, d, J=6.9 Hz), 1.04 (3H, d, J=6.9 Hz), 2.03–1.47 (1H, m), 2.92–3.05 (3H, m), 3.43 (1H, dd, J=11.5, 7.6 Hz), 4.22–4.33 (1H, m), 4.97–5.13 (1H, m), 5.09 (2H, s), 5.84 (1H, d, J=9.1 Hz), 6.11 (1H, brs), 6.47 (1H, dd, J=9.1, 3.0 Hz), 7.34 (5H, s).

EXAMPLE 25

4S-[R-(4S-ethyl-1,3-thiazolidine-2-thion-3-ylcarbonyl)phthalimidomethyl]azetidin-2-one:

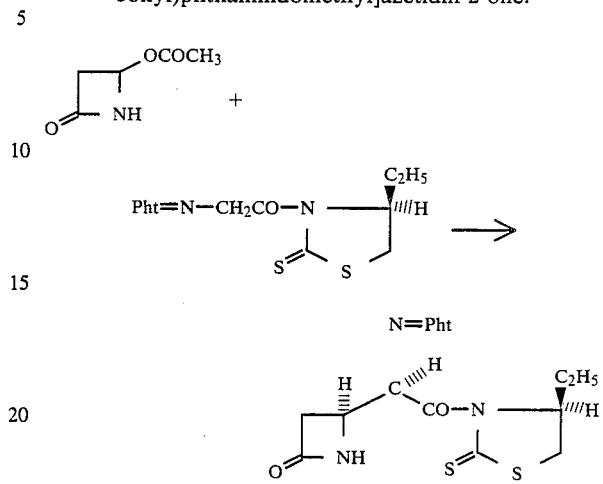

By operating as in Example 18 except that the enolation was carried out at 0° C. for 1 hour and the reaction of the resulting enol with the azetidinone was carried out at 0° C. for 1 hour, the captioned compound was obtained in a yield of 72.1%.

IR(CHCl$_3$): 1760, 1720, 1690 cm$^{-1}$

NMR(CDCl$_3$)δ: 1.02 (3H, t, J=7.4 Hz), 1.76–2.15 (2H, m), 2.85–3.20 (3H, m), 3.62 (1H, dd, J=1.14, 7.5 Hz), 4.16–4.32 (1H, m), 6.20 (1H, brs), 6.34 (1H, d, J=5.6 Hz), 7.69–7.92 (4H, m).

EXAMPLE 26

3S-(1R-t-butyldimethylsilyloxyethyl)-4S-[R-(4S-ethyl-1,3-thiazolidine-2-thion-3-ylcarbonyl)methylthiomethyl]azetidin-2-one:

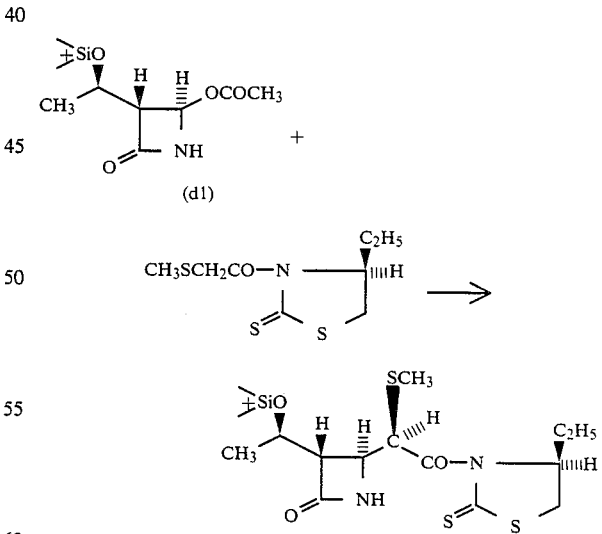

By operating as in Example 21 using a 4-acetoxy-3α-(1β-t-butyldimethylsiloxyethyl)azetidin-2-one (DL), the captioned compound was obtained in a yield of 38.2%.

IR(CHCl$_3$): 1755, 1680 cm$^{-1}$

NMR(CDCl$_3$)δ: 0.07 (6H, s), 0.80 (9H, s), 1.03 (3H, t, J=7.7 Hz), 1.17 (3H, d, J=6.3 Hz), 1.77–2.03 (2H, m), 2.14 (3H, s), 3.00 (1H, dd, J=11.6, 1.2 Hz), 3.20–3.33 (1H, m), 3.62 (1H, dd, J=11.6, 8.1 Hz), 4.12–4.38 (2H, m), 4.85–5.09 (1H, m), 5.93 (1H, d, J=6.9 Hz), 6.17 (1H, brs).

EXAMPLE 27

3S-(1R-t-butyldimethylsilyloxyethyl)-4S-[R-(4S-isopropyl1,3-thiazolidine-2-thion-3-ylcarbonyl)benzyloxycarbonylaminomethyl]azetidin-2-one:

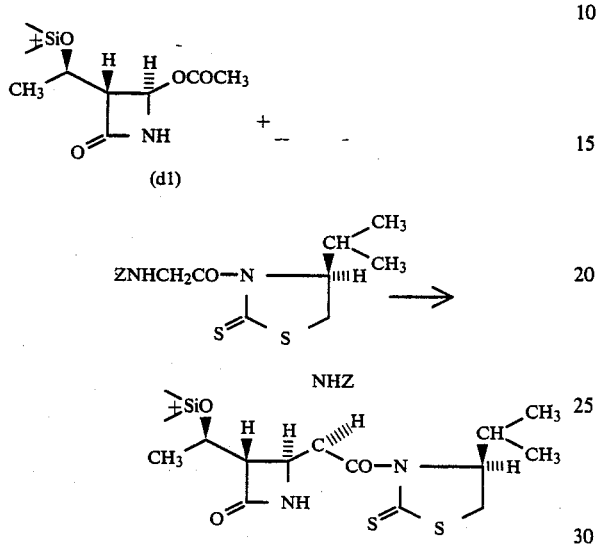

By operating as in Example 24 using 4-acetoxy-3S-(1R-t-butyldimethylsilyloxyethyl)azetidin-2-one, the captioned compound was obtained in a yield of 78%.
IR(CHCl₃): 1760, 1720, 1680.
NMR(CDCl₃)δ: 0.05 (3H, s), 0.07 (3H, s), 0.84 (9H, s), 0.93 (3H, d, J=6.9 Hz), 1.03 (3H, d, J=6.9 Hz), 1.26 (3H, d, J=6.9 Hz), 2.05–2.45 (1H, m), 2.92–3.23 (2H, m), 3.30–3.60 (1H, m), 4.03–4.30 (2H, m), 5.06 (2H, s), 5.03–5.20 (1H, m), 5.70 (1H, d, J=8.4 Hz), 5.97 (1H, brs), 6.61 (1H, dd, J=8.4, 3.1 Hz), 7.33 (5H, s).

EXAMPLE 28

3S-(1R-t-butyldimethylsilyloxyethyl)-4S-[(4S-isopropyl-1,3-thiazolidine-2-thion-3-ylcarbonyl)benzyloxymethyl]azetidin2-one:

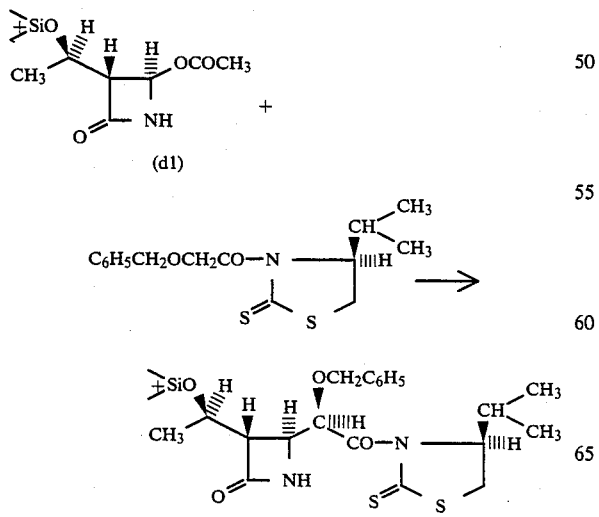

By operating as in Example 22 using 4-acetoxy-3S-(1R-t-butyldimethylsilyloxyethyl)azetidin-2-one , the captioned compound was obtained in a yield of 73.4%.
IR(CHCl₃): 1755, 1690 cm⁻¹
NMR(CDCl₃)δ: 0.05 (6H, s), 0.08 (9H, s), 0.90 (3H, d, J=7.4 Hz), 1.00 (3H, d, J=7.4 Hz), 1.12 (3H, d, J=7.4 Hz), 2.0–2.4 (1H, m), 2.93 (1H, dd, J=11.6, 1.2 Hz), 3.18 (1H, dd, J=11.6, 8.1 Hz), 3.30–3.45 (1H, m), 4.1–4.3 (2H, m), 4.46 (1H, d, J=11.4 Hz), 4.65 (1H, d, J=11.4 Hz), 4.8–5.0 (1H, m), 5.86 (1H, brs), 6.22 (1H, d, J=5.0 Hz), 7.33 (5H, s).

EXAMPLE 29

3S-(1R-t-butyldimethylsilyloxyethyl)-4S-[1R-1-(1,3-thiazolidine-2-thion-3-yl)carbonylethyl]azetidin-2-one:

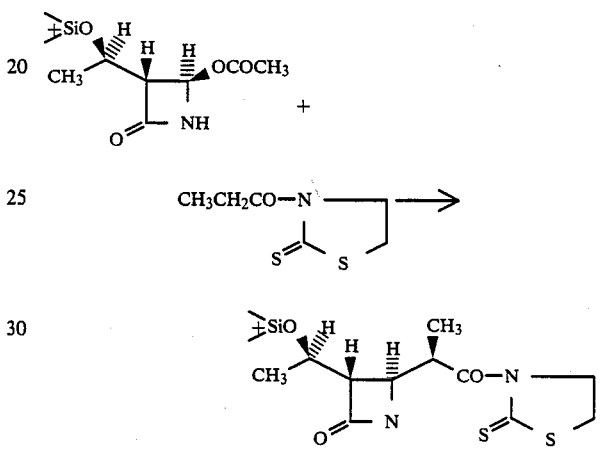

By operating as in Example 1 using 4-acetoxy-3S-(1R-t-butyldimethylsilyloxyethyl)azetidin-2-one and 3-propionyl-1,3-thiazolidine-2-thione, the captioned compound was obtained in a yield of 80%.
NMR(CDCl₃)δ: 0.07 (s, 6H), 0.88 (s, 9H), 1.21 (d, 3H, J=6.0 Hz), 1.26 (d, 3H, J=6.0 Hz), 3.30 (dd, 1H, J=5.0, 2.0 Hz), 3.28 (t, 2H, J=7.5 Hz), 3.94 (dd, 1H, J=5.0, 3.0 Hz), 4.18 (m, 1H), 4.55 (t, 2H, J=7.5 Hz), 4.95 (m, 1H), 6.24 (bs, 1H).

EXAMPLE 30

3S-(1R-t-butyldimethylsilyloxyethyl)-4R-[1R-1-4S-4-ethyl(1,3-thiazolidine-2-thion-3-yl)carbonylethyl]azetidin-2-one:

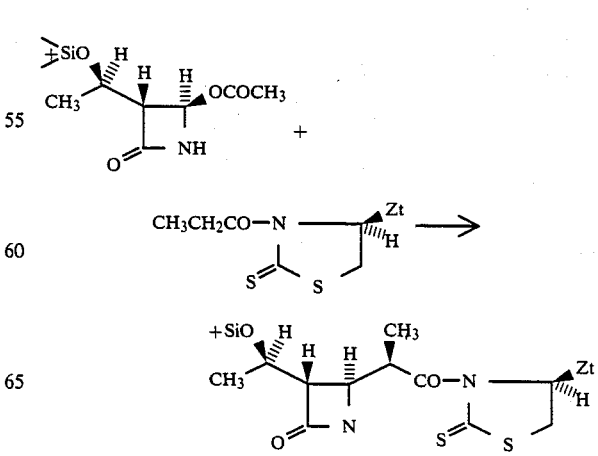

By operating as in Example 1 using 4-acetoxy-3S-(1R-t-butyldimethylsilyloxyethyl)azetidin-2-one and 3-propionyl-4S-4-ethyl-1,3-thiazolidine-2-thione, the captioned compound was obtained in a yield of 80%.

$^1$H-NMR(δppm, CDCl$_3$): 0.07 (s, 6H), 0.90 (s, 9H), 1.00 (t, 3H, J=8.0 Hz), 1.23 (d, 3H, J=6 Hz), 1.26 (d, 3H, J=6 Hz), 1.6–2.03 (m, 2H), 2.90 (dd, 1H, J=11.0, 1.0 Hz), 3.07 (m, 1H), 3.50 (dd, 1H, J=11.0, 7.0 Hz), 3.95 (m, 1H), 4.0–4.30 (m, 1H), 4.90–5.20 (m, 2H), 6.10 (bs, 1H).

$[α]_D^{25}$: +233.9° (c 0.77, CHCl$_3$)

m.p.: 85.5°–86.5° C.

REFERENTIAL EXAMPLE 1

3S-(1R-tert-butyldimethylsilyloxyethyl)-4R-carboxymethylazetidin-2-one:

3S-(1R-tert-Butyldimethylsilyloxyethyl)-4R-[(4S-ethyl-1,3-thiazolidin-2-one (the main product of Example 1; 60 mg, 0.144 millimole) was dissolved in a mixture of methanol (3 ml) and water (3 ml) and a 1N aqueous solution of sodium hydroxide (0.3 ml) was added. The mixture was stirred at room temperature for 20 minutes. Methanol was evaporated under reduced pressure, and the residue was dissolved in water (20 ml) and washed with chloroform (10 ml). The aqueous layer was acidified with 1N HCl, and extracted three times with ethyl acetate (20 ml). The extract was washed with a saturated aqueous sodium chloride solution (20 ml), and dried over anhydrous sodium sulfate, and the solvent was evaporated under reduced pressure. The residue was purified by silica gel column chromatography (eluent: chloroform/methanol=30/1) to give the captioned compound (29 mg, yield 70%) as a slightly yellow solid.

IR(KBr): 1720 cm$^{-1}$ $^1$H-NMR(δppm, CDCl$_3$): 0.07 (6H, s), 0.87 (9H, s), 1.22 (3H, d, J=6 Hz), 2.51–2.90 (3H, m), 3.82–4.07 (1H, m), 4.08–4.36 (1H, m), 7.11 (1H, brs).

$[α]_D^{25}$: +11.7° (0.65, CHCl$_3$)

REFERENTIAL EXAMPLE 2

3R-(1S-tert-butyldimethylsilyloxyethyl)-4S-carboxymethylazetidin-2-one:

As in Referential Example 1, the captioned compound was obtained as a slightly yellowish solid (66%) from 3R-(1S-tert-butyldimethylsilyloxyethyl)-4S-[(4S-ethyl-1,3-thiazoline-2-thion-3-yl)carbonylmethyl]azetidin-2-one (the compound obtained in Example 1).

The IR and $^1$H-NMR data of the product agreed with those of the product of Referential Example 1.

$[α]_D^{25}$: −12.0° (c=1.27, CHCl$_3$).

REFERENTIAL EXAMPLE 3

3S-(1S-tert-butyldimethylsilyloxy)ethyl-4R-carboxymethylazetidin-2-one:

As in Referential Example 1, the captioned compound (yield 69.7%) was obtained as a slightly white solid from 3S-(1S-tert-butyldimethylsilyloxyethyl)-4R-[(4-S-ethyl-1,3-thiazoli dine-2-thion-3-yl)carbonylmethyl]azetidin-2-one (the main product of Example 3).

Melting point: 137.9°–138.0° C.

IR(KBr): 1710 cm$^{-1}$ $^1$H-NMR(δppm, CDCl$_3$): 0.07 (6H, s), 0.89 (9H, s), 1.30 (3H, d, J=6 Hz), 2.50–2.76 (2H, m), 2.88–3.00 (1H, m), 3.73–3.96 (1H, m), 4.02–4.35 (1H, m), 6.93 (1H, brs).

$[α]_D^{25}$: +42.3° (C 1.01, CHCl$_3$)

The absolute configuration indicated above was determined by X-ray crystal analysis.

REFERENTIAL EXAMPLE 4

3S-(1S-tert-butyldimethylsiloxyethyl)-4R-(3-p-nitrobenzyloxycarbonyl-2-oxopropyl)azetidin-2-one:

Mono-p-nitrobenzyl malonate (239.1 mg: 1 millimole) and magnesium ethoxide (57.2 mg; 0.5 millimole) were dissolved in anhydrous tetrahydrofuran (2ml), and the solution was stirred at room temperature for 1 hour in an argon atmosphere. The solvent was evaporated under reduced pressure, and the residue was dissolved in tetrahydrofuran (2 ml). The solution was added to a solution of 3S-(1S-tert-butyldimethylsilyloxyethyl)-4R-carboxymethylazetidin-2-one (115 mg; 0.4 millimole) and carbonyldiimidazole (71.3 mg; 0.44 mmole) in anhydrous tetrahydrofuran (3 ml) which had previously been stirred at room temperature for 3 hours in an argon atmosphere. The mixture was stirred at room temperature for 19 hours. The solvent was evaporated under reduced pressure. Diethyl ether (30 ml) was added to the residue, and the mixture was washed with 0.1N HCl (10 ml). The aqueous layer was extracted with diethyl ether (10 ml), and the combined ethereal layers were washed with a saturated aqueous sodium chloride solution, and dried over anhydrous sodium sulfate, and the solvent was evaporated under reduced pressure. The residue was subjected to column chromatography (silica gel 10 g; eluent: chloroform/ethyl acetate=4/1) to give the captioned compound (140 mg, yield 75.6%) as a slightly yellow oil.

$[α]_D^{25}$: +32.7° (C 0.97, CHCl$_3$)

IR(neat): 1750, 1720, 1525 1350 cm$^{-1}$ $^1$H-NMR(δppm, CDCl$_3$): 0.07 (6H, s), 0.87 (9H, s), 1.28 (3H, d, J=6 Hz), 2.80–2.96 (3H, m), 3.56 (2H, s), 3.73–3.99 (1H, m), 4.02–4.34 (1H, m), 5.26 (2H, s), 5.96 (1H, brs), 7.52 (2H, d, J=9 Hz), 8.24 (2H, d, J=9 Hz).

What is claimed is:

1. A process for producing an azetidin-2-one derivative represented by the following formula (I)

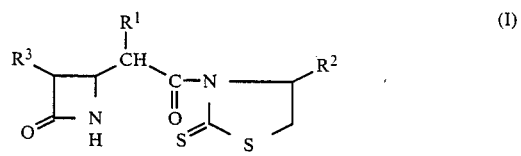

wherein R$^1$ represents a hydrogen atom, a lower alkyl group, an aralkyl group, a lower alkoxy group, aralkoxy group, a lower alkylthio group, an aralkylthio group, or a protected amino group, R$^2$ represents a lower alkyl group, an aryl group or an aralkyl group, and R$^3$ represents a hydrogen atom or a group of the formula

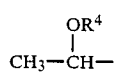

in which R$^4$ represents a hydrogen atom or a protective group for the hydroxyl group, which comprises reacting a compound represented by the following formula (II)

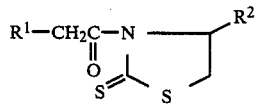 (II)

wherein $R^1$ and $R^2$ are as defined, with tin (II) triflate in the presence of a base, and then reacting the resulting compound with a compound represented by the following formula (III)

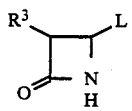 (III)

wherein $R^3$ is as defined, and L represents a lower alkanoyloxy group, a lower alkylsulfonyl group or an arylsulfonyl group.

2. The process for producing an azetidin-2-one derivative according to claim 1 wherein a compound represented by the following formula (Ia)

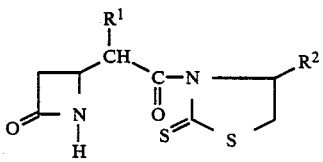 (Ia)

wherein $R^1$ and $R^2$ are as defined in claim is produced by using a compound of the following formula (IIIa)

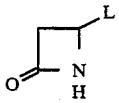 (III-a)

wherein L is as defined in claim 1, as the compound of formula (III).

3. The process for producing an azetidin-2-one derivative according to claim 1 wherein a compound represented by the following formula (Ib)

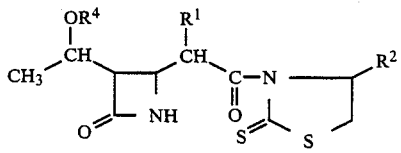 (Ib)

wherein $R^1$, $R^2$ and $R^4$ are as defined in claim 1 is produced by using a compound of the following formula (IIIb)

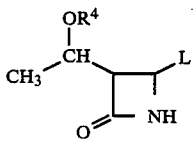 (IIIb)

wherein $R^4$ and L are as defined in claim 1, as the compound of formula (III).

4. The process according to claim 1 wherein the compound represented by formula (I) is in the form of an optically active compound or a mixture of diastereomers.

5. The process according to claim 1 wherein each of $R^1$, $R^2$ and $R^3$ has an R- or S-configuration.

6. The process according to claim 1 wherein each of $R^1$ and $R^2$ has an R- or S-configuration.

7. The process according to claim 1 wherein each of $R^1$, $R^2$ and $OR^4$ has an R- or S-configuration.

8. The process according to claim 1 wherein the side chain has an R- or S-configuration.

9. The process according to claim 3 wherein a racemate of the threo form represened by the following formula (IIIc)

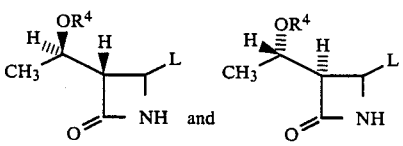 (IIIc)

wherein L and $R^1$ are as defined in claim 3, is used as the compound of formula (IIIb).

10. The process according to claim 3 wherein a racemate of the erythro form represented by the following formula (IIId)

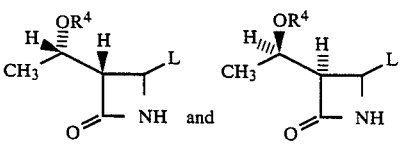 (IIId)

wherein L and $R^4$ are as defined in claim 3, is used as the compound of formula (IIIb).

* * * * *